(12) United States Patent
Hang et al.

(10) Patent No.: US 10,576,211 B2
(45) Date of Patent: Mar. 3, 2020

(54) MEDICATION DISPENSING SYSTEM

(71) Applicant: Becton, Dickinson and Company, Franklin Lakes, NJ (US)

(72) Inventors: Tianqi Hang, Orange, NJ (US); Uzair Siddiqui, Jersey City, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/051,249

(22) Filed: Jul. 31, 2018

(65) Prior Publication Data
US 2019/0221301 A1 Jul. 18, 2019

Related U.S. Application Data

(60) Provisional application No. 62/616,688, filed on Jan. 12, 2018.

(51) Int. Cl.
| | |
|---|---|
| *A61M 5/315* | (2006.01) |
| *A61M 5/28* | (2006.01) |
| *A61J 1/20* | (2006.01) |
| *B65B 3/00* | (2006.01) |
| *G16H 20/13* | (2018.01) |

(Continued)

(52) U.S. Cl.
CPC ........ *A61M 5/31546* (2013.01); *A61J 1/2096* (2013.01); *A61M 5/28* (2013.01); *A61M 5/3129* (2013.01); *A61M 5/31566* (2013.01); *B65B 3/003* (2013.01); *G16H 20/13* (2018.01); *G16H 20/17* (2018.01); *A61M 5/178* (2013.01); *A61M 5/482* (2013.01); *A61M 2005/3125* (2013.01); *A61M 2205/3569* (2013.01); *A61M 2205/3584* (2013.01); *A61M 2205/502* (2013.01)

(58) Field of Classification Search
CPC .................................................... A61J 1/2096
See application file for complete search history.

(56) References Cited

U.S. PATENT DOCUMENTS

| | | | |
|---|---|---|---|
| 6,213,996 B1 | 4/2001 | Jepson et al. | |
| 6,877,530 B2 | 4/2005 | Osborne et al. | |

(Continued)

FOREIGN PATENT DOCUMENTS

| | | | |
|---|---|---|---|
| AU | 2013219198 B2 | | 9/2013 |
| WO | PCTUS2015/050014 | * | 9/2015 |

OTHER PUBLICATIONS

Peter Loftus, Eli Lilly Bets Big on Insulin-Delivery Devices, Nov. 21, 2017, The Wall Street Journal, retrieved from URL: https://www.wsj.com/articles/eli-lilly-bets-big-on-insulin-delivery-devices-1511269200 (3 Pages Total).

*Primary Examiner* — Nabil H Syed
*Assistant Examiner* — Cal J Eustaquio
(74) *Attorney, Agent, or Firm* — Dickinson Wright PLLC

(57) ABSTRACT

A medication dispensing system configured to prepare a plurality of syringes for medication delivery, the system comprising a turntable carrying a plurality of medication vials, each medication vial being engaged to a smart vial adapter, a translation stage carrying a plurality of syringes, a base having a plurality of arms configured to interact with the plurality of syringes, and a processor that is programmed to rotate the turntable, axially move the translation stage and operate the plurality of arms such that a selected syringe of the plurality of syringes engages a selected medication vial of the plurality of medication vials to draw medicament.

17 Claims, 23 Drawing Sheets

(51) Int. Cl.
*G16H 20/17* (2018.01)
*A61M 5/31* (2006.01)
A61M 5/48 (2006.01)
A61M 5/178 (2006.01)

(56) References Cited

U.S. PATENT DOCUMENTS

| | | | |
|---|---|---|---|
| 8,286,671 B1 | 10/2012 | Strangis | |
| 8,632,738 B2 | 1/2014 | Giribona et al. | |
| 8,807,131 B1* | 8/2014 | Tunnell | A61M 16/0051 |
| | | | 128/200.23 |
| 9,180,257 B2 | 11/2015 | Walters et al. | |
| 2004/0010425 A1* | 1/2004 | Wilkes | A47B 81/00 |
| | | | 705/3 |
| 2008/0114328 A1* | 5/2008 | Doherty | A61J 1/2096 |
| | | | 604/414 |
| 2009/0036764 A1 | 2/2009 | Rivas et al. | |
| 2009/0108018 A1 | 4/2009 | Li et al. | |
| 2011/0253139 A1 | 10/2011 | Guthrie et al. | |
| 2012/0095415 A1 | 4/2012 | Sharvit et al. | |
| 2012/0323208 A1 | 12/2012 | Bochenko et al. | |
| 2014/0324021 A1 | 10/2014 | Ulrich et al. | |
| 2017/0151127 A1 | 6/2017 | Einy et al. | |
| 2017/0286638 A1* | 10/2017 | Searle | A61M 5/16804 |
| 2018/0036495 A1 | 2/2018 | Searle et al. | |

* cited by examiner

MEDICATION DISPENSING SYSTEM

CROSS-REFERENCE TO RELATED APPLICATION

This application claims priority under 35 U.S.C. 119(e) to U.S. provisional application Ser. No. 62/616,688, filed on Jan. 12, 2018, which is incorporated herein in its entirety.

FIELD OF THE INVENTION

The present invention relates generally to a medication dispensing system that prepares a plurality of syringes for medication delivery.

BACKGROUND OF THE INVENTION

Effective administration of drug injections, particularly in the case of insulin used by diabetics, requires that the drug be kept under proper storage conditions and that a record of all administered doses be kept. While education is offered for home injection patients, most patients still find it challenging to follow the instructions properly on a daily basis.

Health care personnel can record dose-related information in a clinical setting, but there is significant overhead associated with capturing this information. It is also difficult to measure and record certain parameters that can affect the safety and efficacy of the drug, such as drug temperature and proper mixing.

Further, health care personnel are often responsible for many patients, various medications and different injection schedules. Accordingly, health care personnel find the current systems to be burdensome, laborious and prone to human error.

The present invention addresses this opportunity by providing a medication dispensing system to prepare a plurality of syringes and incorporating a vial adapter with electronic components that allow it to perform these and/or other functions.

SUMMARY OF EMBODIMENTS OF THE INVENTION

In accordance with embodiments of the present invention, a medication dispensing system using a smart vial adapter to prepare a plurality of syringes is provided that is capable not only of providing physical access to a drug vial, but also of performing dose capture, condition monitoring and information reporting functions. These functions can include measuring the dose drawn from the vial, measuring the time of a dose capture event, monitoring the vial temperature, measuring the amount of motion or perturbation the vial is subjected to, capturing various other parameters that can provide additional insights associated with the drug or the amount of the dose being drawn from the vial, and communicating the recorded information to a companion application on a computer, smartphone or other device. In addition, each of the plurality of syringes is automatically prepared according to specific parameters to reduce labor and stress to health care personnel and increases accuracy due to the automation.

More specifically, one embodiment of the present invention relates to a medication dispensing system configured to prepare a plurality of syringes for medication delivery, the system comprising a turntable carrying a plurality of medication vials, each medication vial being engaged to a smart vial adapter, a translation stage carrying a plurality of syringes, a base having a plurality of arms configured to interact with the plurality of syringes, and a processor that is programmed to rotate the turntable, axially move the translation stage and operate the plurality of arms such that a selected syringe of the plurality of syringes engages a selected medication vial of the plurality of medication vials to draw medicament.

Another embodiment of the present invention provides a method of preparing a plurality of syringes for medication delivery, the method comprising rotating a turntable to align a selected medication vial of a plurality of medication vials, translating a translation stage linearly to align a selected syringe of a plurality of syringes to the selected medication vial, removing a shield of the selected syringe, moving the selected syringe toward the selected medication vial, piercing a septum of the selected medication vial with a needle of the selected syringe, transferring medicament from the selected medication vial to the selected syringe, and disengaging the selected syringe from the selected medication vial.

BRIEF DESCRIPTION OF THE DRAWINGS

Aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Figure 1:
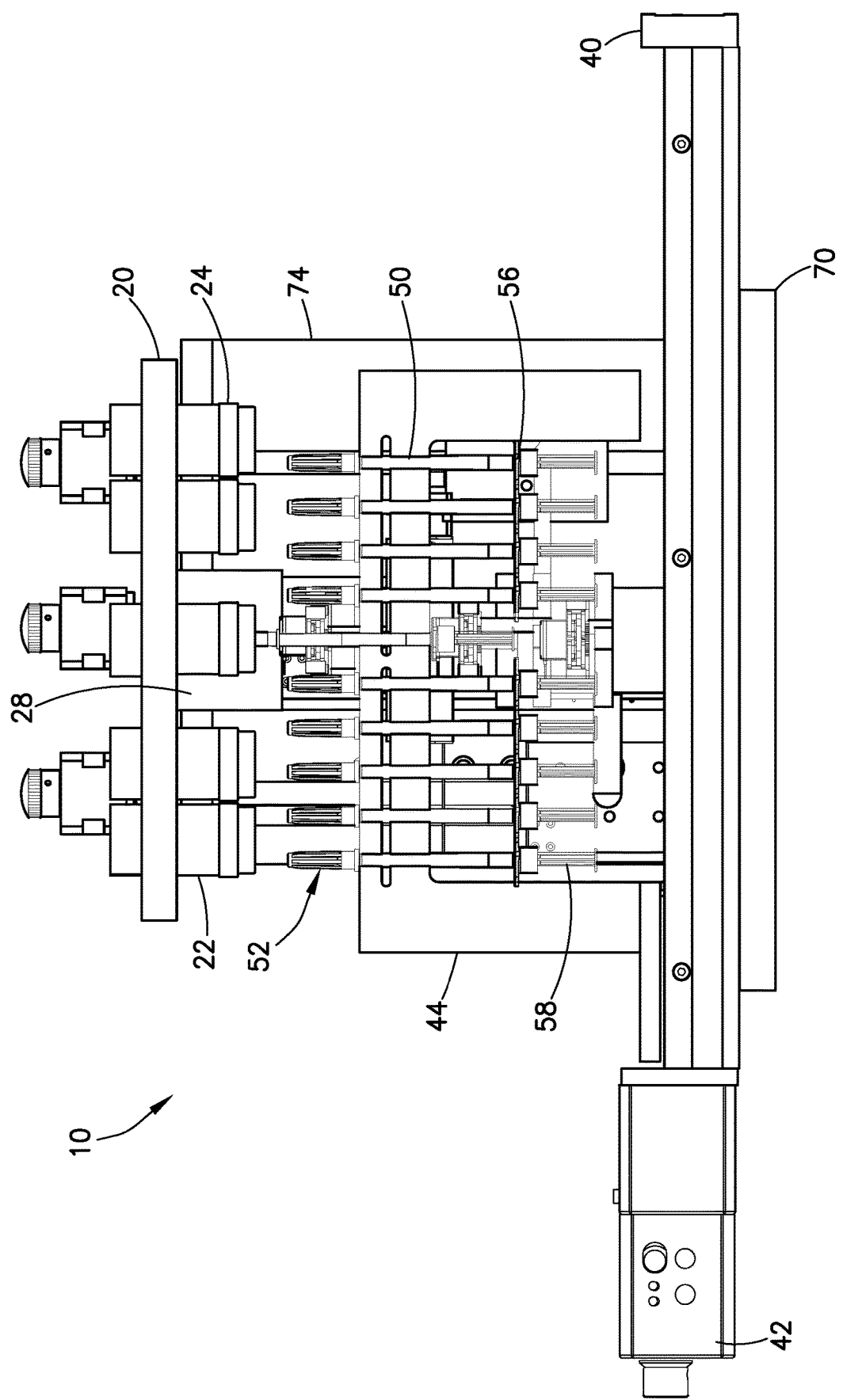
FIG. 1 illustrates a front view of a medication dispensing system of the first embodiment.

Reference will now be made in detail to embodiments of the present invention, which are illustrated in the accompanying drawings, wherein like reference numerals refer to like elements throughout. The embodiments described and illustrated herein exemplify, but do not limit, the present invention, and the drawings are not necessarily to scale with respect to each other or with respect to actual physical embodiments. Further, it will be understood by one skilled in the art that the phraseology and terminology used herein is for the purpose of description and should not be regarded as limiting.

The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

Further, as used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

Figure 2:
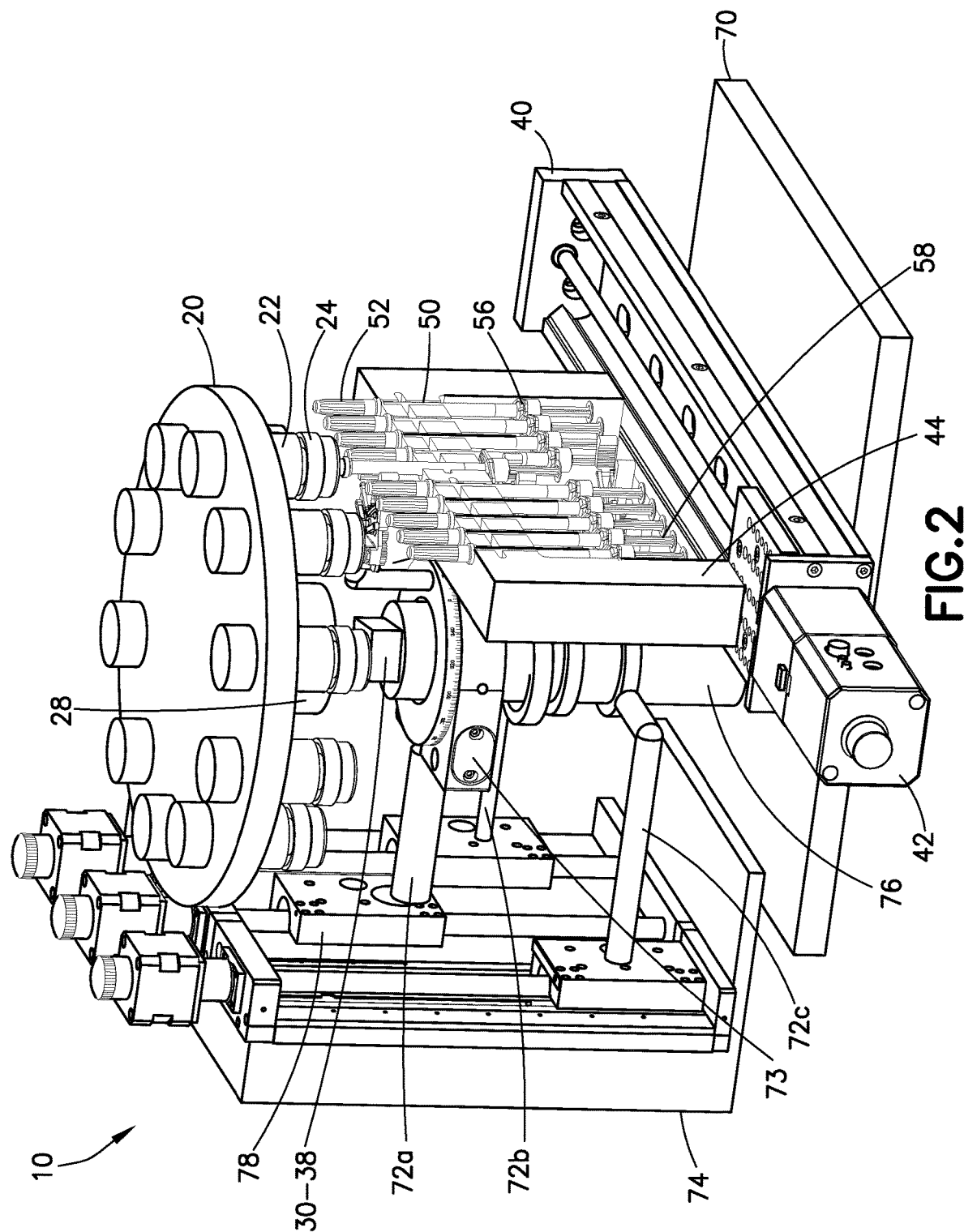
FIG. 2 illustrates a right side perspective view of the medication dispensing system of FIG. 1.
Figure 3:
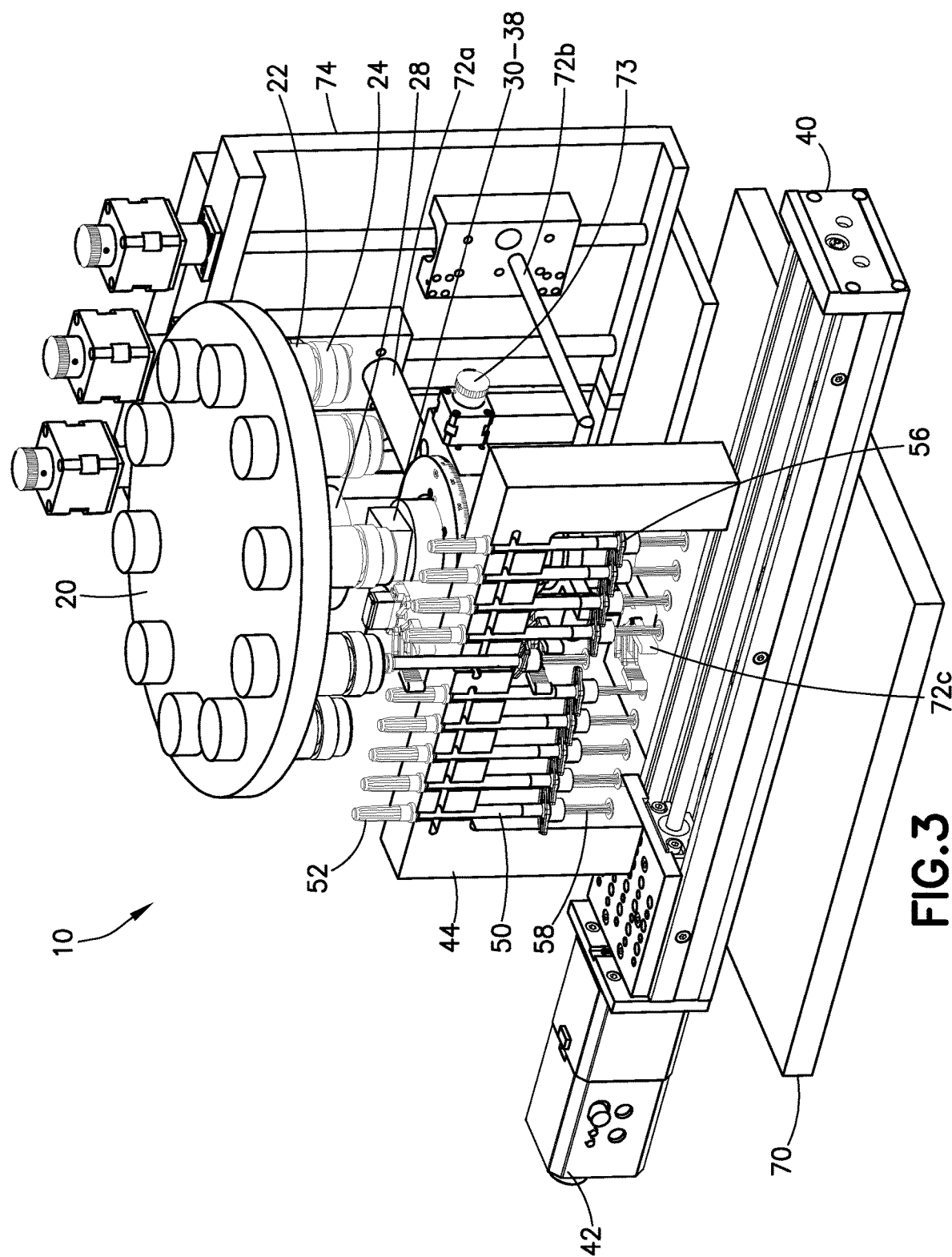
FIG. 3 illustrates a left side perspective view of the medication dispensing system of FIGS. 1 and 2.
Figure 4:
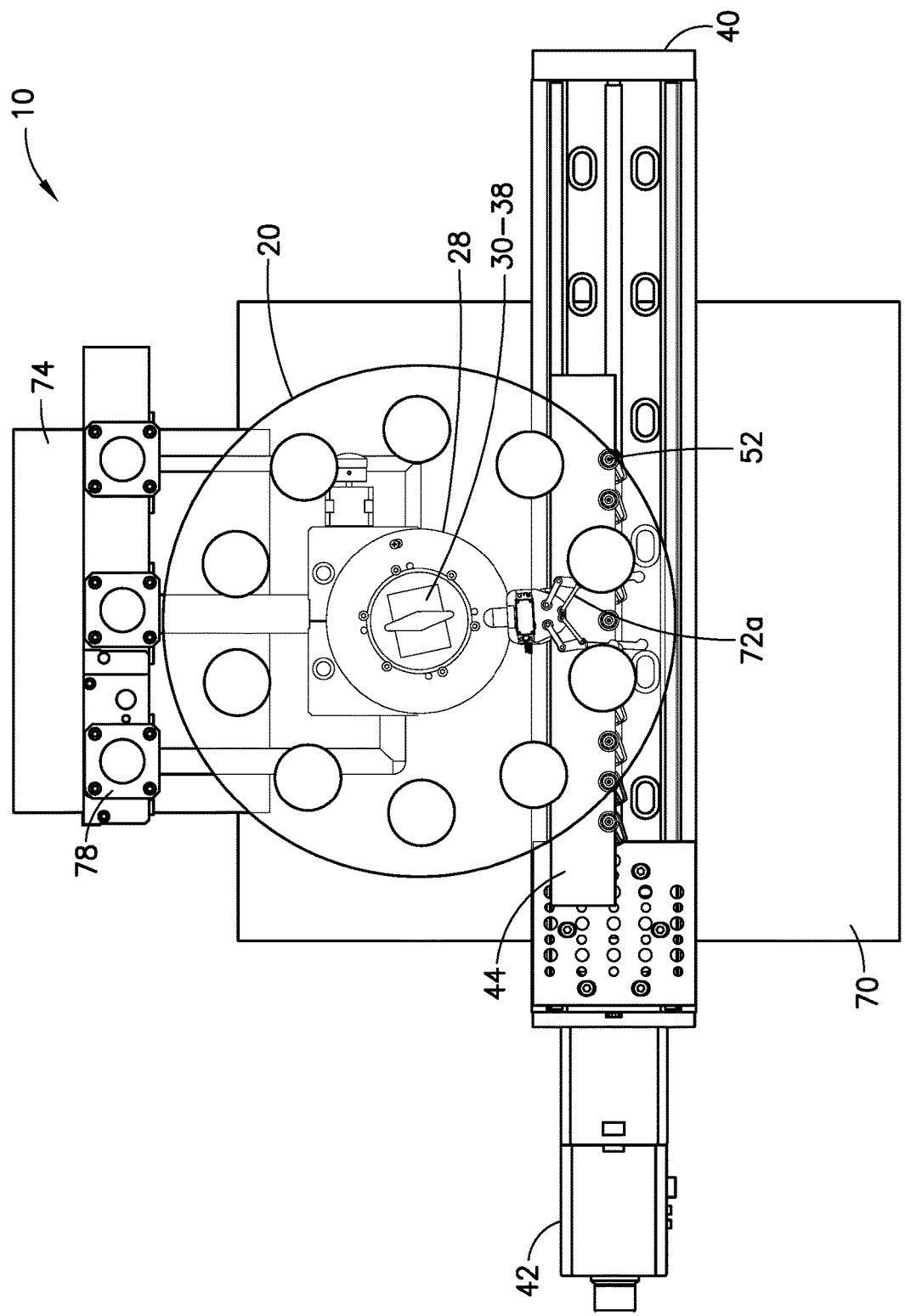
FIG. 4 illustrates a top view of the medication dispensing system with a transparent turntable of FIGS. 1-3.
Figure 5:
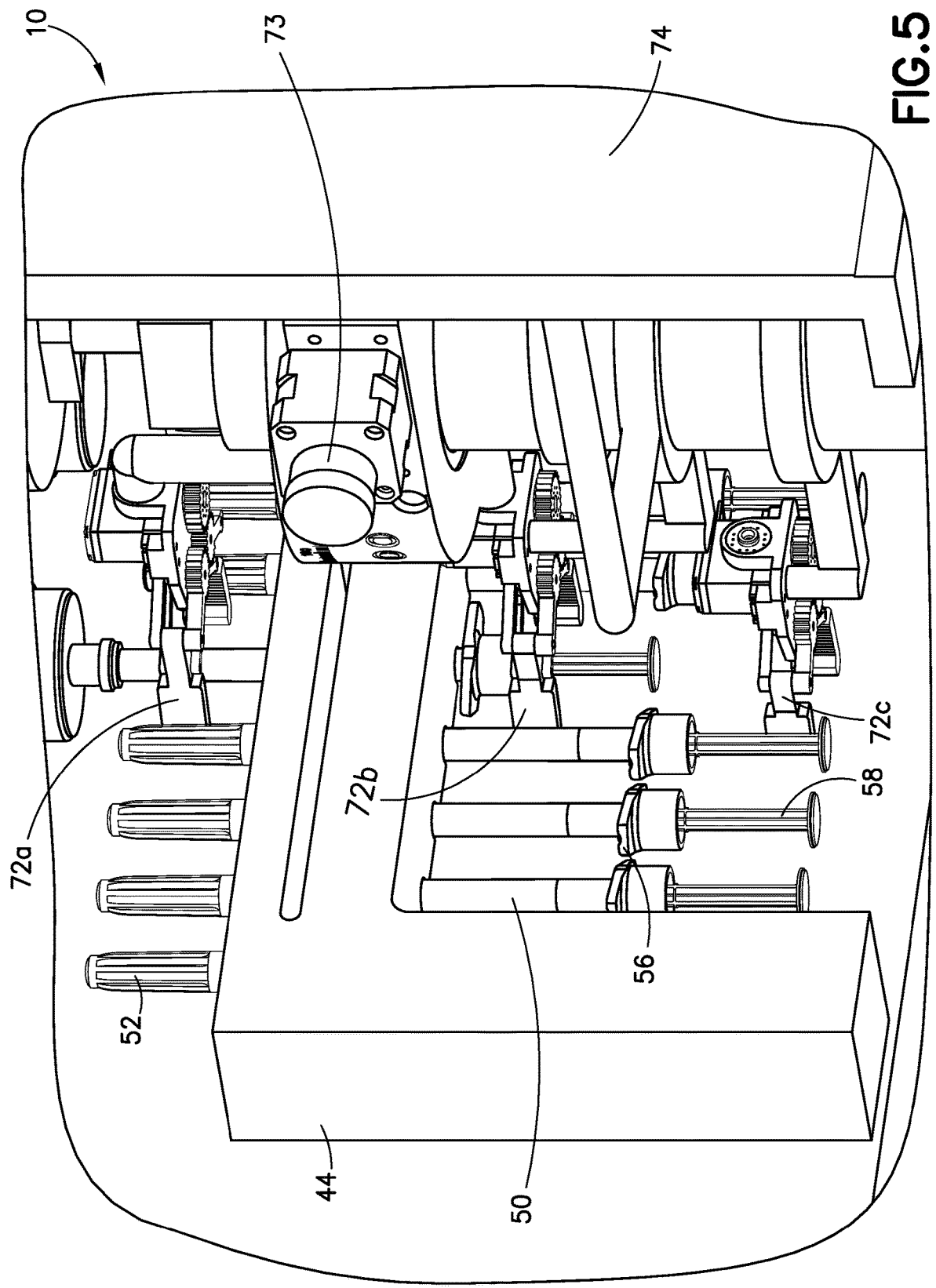
FIG. 5 illustrates a left side perspective view of arms in a base of the medication dispensing system of FIGS. 1-4.
Figure 6:
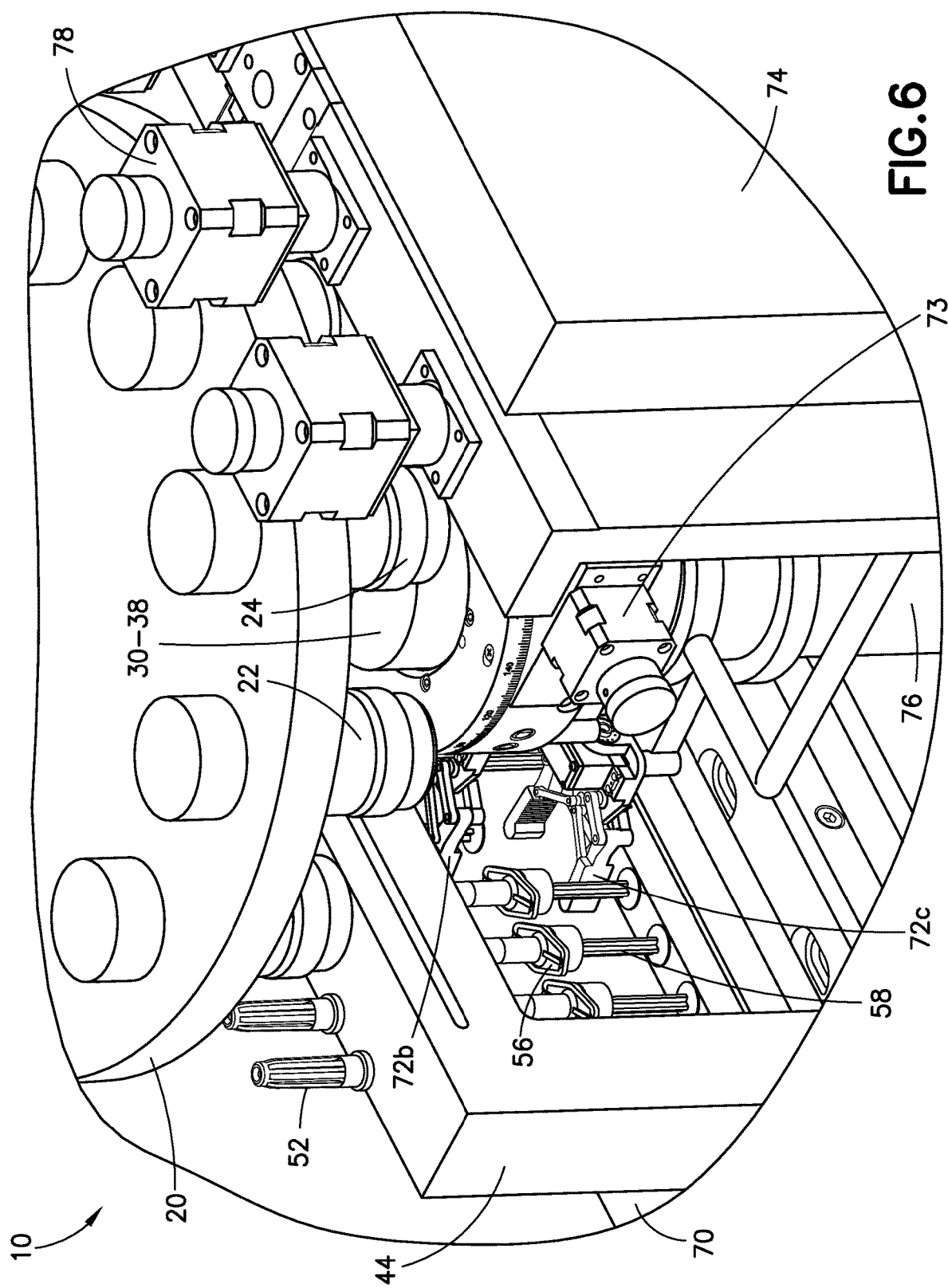
FIG. 6 illustrates an elevated left side perspective view of the turntable and the arms in the base of the medication dispensing system of FIGS. 1-5.

FIGS. 1-7 illustrate various views of the medication dispensing system 10. The medication dispensing system 10 includes a turntable 20 carrying a plurality of medication vials 22. As best illustrated in FIG. 4, the turntable 20 is substantially circular in shape and rotates on its central axis. The turntable 20 includes a plurality of openings, each of which carry one of a plurality of medication vials 22. The plurality of medication vials 22 are arranged in a substantially circular configuration centered on the same central axis of the turntable 20. The plurality of medication vials 22 are disposed adjacent to an outer circumference of the turntable 20, and contains a medicament such as insulin or another injectable drug in liquid form.

Figure 11:
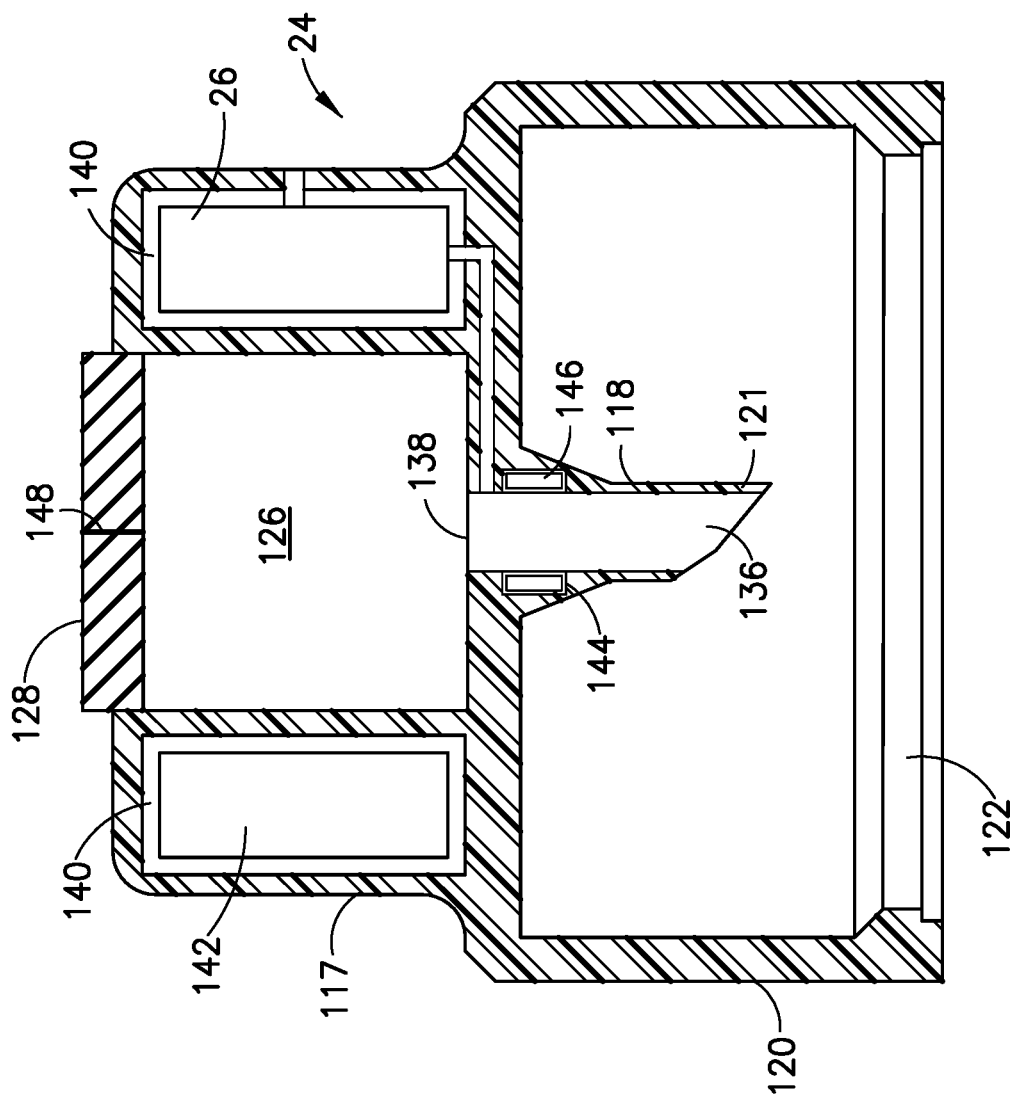
FIG. 11 illustrates a detailed cross-sectional view of the smart vial adapter, shown detached from the medication vial of FIG. 10.

Each of the medication vials 22 is connected to a smart vial adapter 24 with an internal air pump 26 (See FIG. 11). The air pump 26 supplies filtered air under pressure to the inside of the medication vial 22 via a pump passage 27, corresponding to a specified dose. Specifically, the medication dispensing system 10 can be programmed to provide a specific amount of medicament to the syringe 50 based on the amount of air pressure placed into the medication vial 22 by the air pump 26. Accordingly, the difference in air pressure between the medication vial 22 and the atmospheric pressure drives medicament from the medication vial 22 and into the syringe 50. An exemplary air pump 26 used in this embodiment is a DC 1.5V-6V 3V Transparent Mini Air Pump Micro DC Motor Oxygen Pump 130 mA 300 mmHg. Further description of the operation of the air pump 26 is described below.

A stepper motor 28 is fixed to a bottom surface of the turntable 20 and engaged with a rotation stage motor 76 to support and operate the turntable 20. Specifically, the turntable 20 is configured to rotate to align one of the medication vials 22 with one of the syringes 50. Further description of the operation of the turntable 20 is described below.

Figure 10:
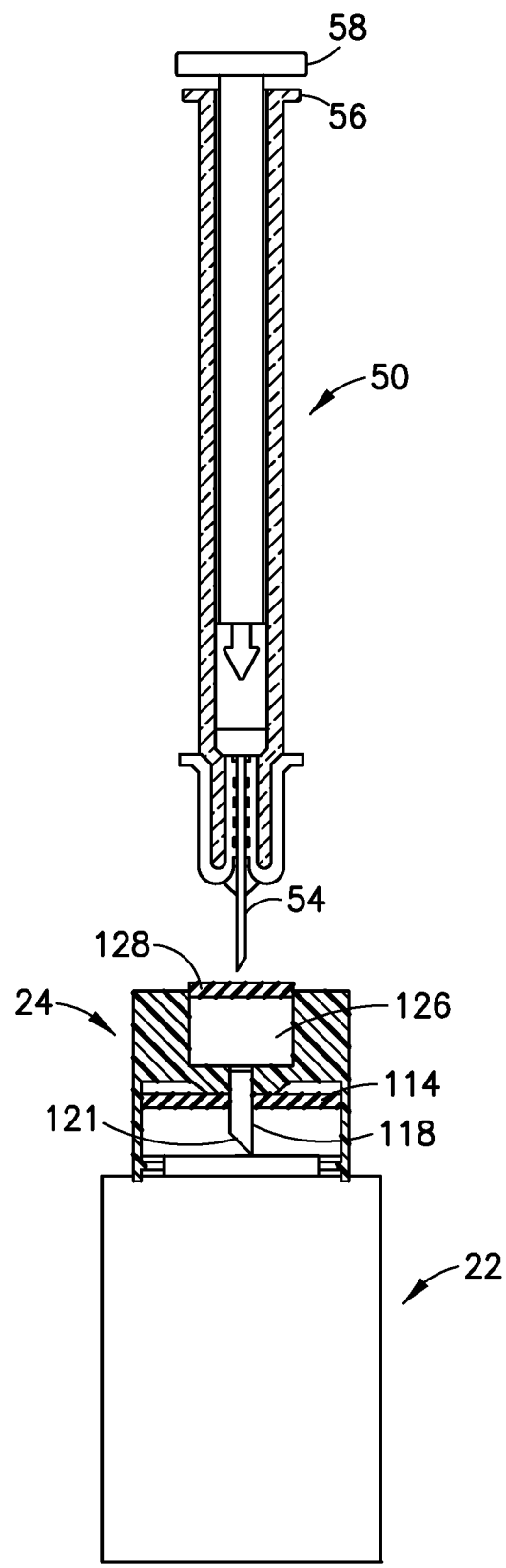
FIG. 10 illustrates a smart vial adapter attached to a medication vial and a syringe positioned for drawing a dose from the medication vial through the smart vial adapter of FIGS. 1-9.
Figure 12:
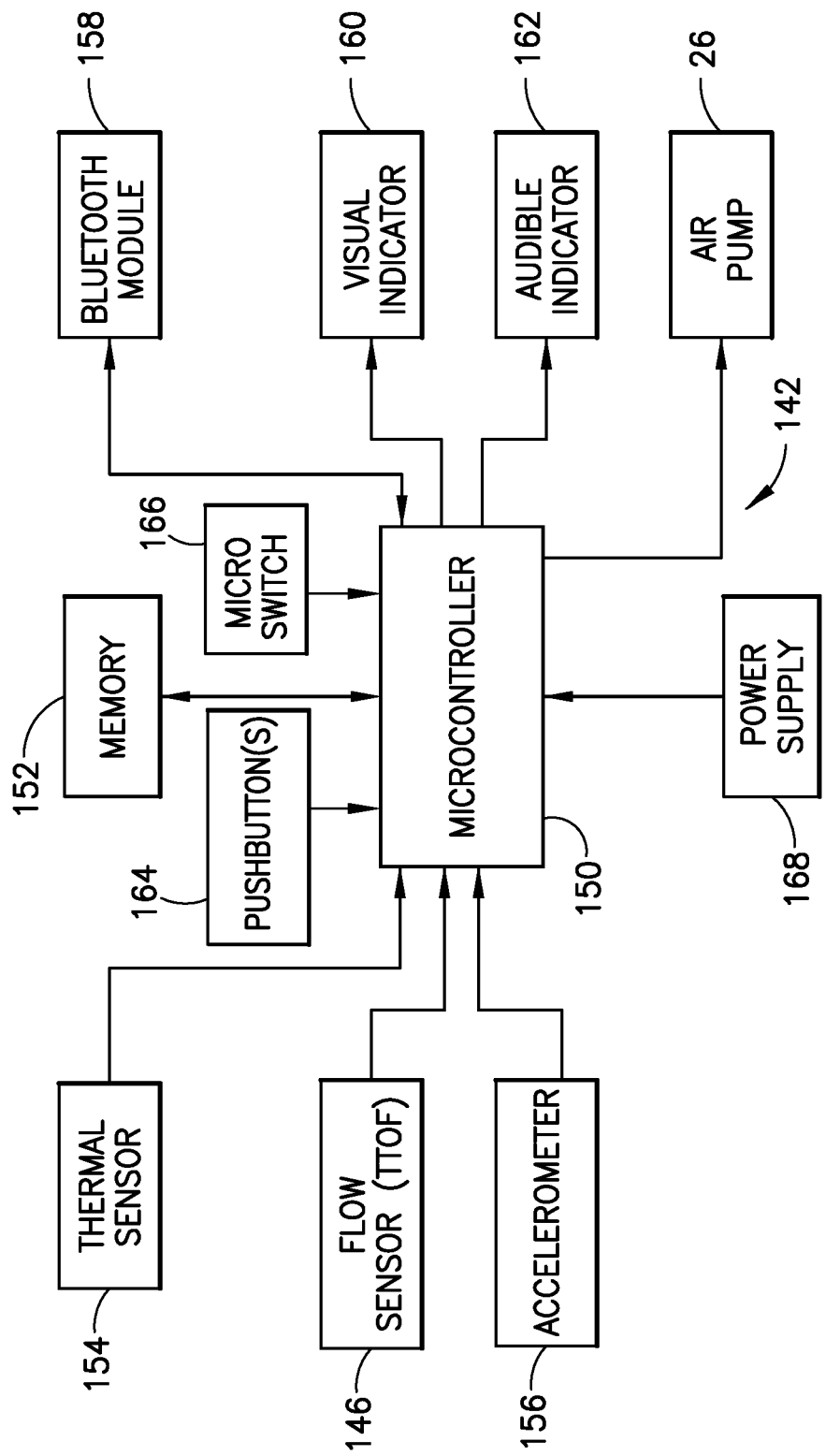
FIG. 12 illustrates a schematic diagram of the electronic components within the smart vial adapter that perform various dose capture, condition monitoring and information reporting functions of FIG. 11.

FIGS. 10-12 illustrate the smart vial adapter 24, aspects of which are described in more detail in co-pending, commonly assigned U.S. patent application Ser. No. 16/051,177 filed on Jul. 31, 2018, incorporated herein by reference in its entirety.

FIG. 10 is a schematic view the smart vial adapter 24 engaged to the medication vial 22 and configured to engage one of a plurality of syringes 50. An upper cap having a rubber septum 114 seals the medication vial 22. The smart vial adapter 24 wirelessly communicates to a smartphone or other mobile electronic device 32 and is attachable to the medication vial 22. The smart vial adapter 24 has a cylindrical plastic housing 117 and a vial access cannula in the form of a downwardly projecting, hollow plastic spike 118 with a sharp tip 121. The housing 117 is attachable over the cap to provide fluidic access to the interior of the medication vial 22 for filling the syringe 50.

In FIGS. 1-3, 6, 7 and 10, the medication vial 22 and smart vial adapter 24 are shown connected to each other, as they would be during the filling of the syringe 50. In the connected state, the spike 118 penetrates the vial septum 114 in a fluid-tight manner to communicate with the interior of the medication vial 22. In addition, an integral lower skirt 120 of the vial adapter housing 117 is received over the vial cap, and an inwardly projecting stabilizing ring 122 of the skirt 120 is engaged with an annular groove beneath the cap to provide a releasable snap or detent connection between the medication vial 22 and the smart vial adapter 24. The plastic material of the vial adapter housing 117 and skirt 120 is sufficiently flexible and resilient to allow for the releasable snap or detent connection between the medication vial 22 and the smart vial adapter 24.

When the medication vial 22 and the smart vial adapter 24 are connected to each other, the syringe 50 can be filled with a dose of the drug contained in the medication vial 22, via the smart vial adapter 24, in much the same manner as when a syringe is filled from a vial directly. The medication vial 22 and the smart vial adapter 24 allow the liquid drug to flow from the medication vial 22 through the inner lumen of the spike 118 into a cylindrical chamber 126 within the housing 117 of the smart vial adapter 24. A rubber septum 128 seals the chamber 126 to provide sterility and to prevent leakage of air or liquid from (or into) the chamber 126 during syringe filling.

In an embodiment without the air pumps 26, once the chamber 126 is filled, a plunger 58 of the syringe 50 (which is not yet engaged with the smart vial adapter 24) is pulled back to fill the syringe barrel with an amount of air corresponding to the dose of the drug that is to be withdrawn from the medication vial 22. The sharp tip of the hollow metal syringe needle 54 is then pushed through the septum 128 of the smart vial adapter 24, bringing the inner lumen of the hollow needle 136 into fluid communication with the interior of the chamber 126 containing the liquid drug. The plunger 58 of the syringe 50 is then depressed to inject the air into the chamber 126.

Since the connected medication vial 22 is above the smart vial adapter 24, the air will move immediately into the medication vial 22 and the chamber 126 will refill with the liquid drug. As in the conventional syringe filling procedure (i.e., without the smart vial adapter 24), the initial injection of air into the medication vial 22 compensates for the liquid that is to be removed from the medication vial 22 and thus prevents the formation of a vacuum in the medication vial 22 when the syringe 50 is filled. After the air injection, the plunger 58 of the syringe 50 is pulled back once again to withdraw the desired amount of liquid drug from the chamber 126 into the syringe barrel. As the liquid drug is removed from the chamber 126, the sealed chamber 126 refills with an equal amount of liquid drug from the medication vial 22 through the inner lumen of the spike 118. The filled syringe 50 can then be used to inject the drug directly into the body of a patient, or into an IV line through a PRN or other type of medical port.

FIG. 11 illustrates a detailed cross-sectional view of the smart vial adapter 24, shown detached from the medication vial 22. As illustrated, the chamber 126 communicates with the inner lumen 136 of the spike 118 through an opening 138 at the bottom of the chamber 126, allowing air and liquid to move freely in either direction between the chamber 126 and the interior of the medication vial 22. Surrounding the chamber 126 is an annular cavity 140 containing various electronic components 142 that allow the smart vial adapter 24 to perform its dose capture, condition monitoring and information reporting functions, as discussed in more detail hereinafter. One or more access doors or plates (not shown) can be provided to allow the components 142 to be installed in the cavity 140 during initial manufacture of the smart vial adapter 24, and to allow for replacement of the battery that powers these components.

The air pump 26 is disposed adjacent to the chamber 126 and within the annular cavity 140 to supply pressure inside the medication vial 22. Specifically, an air pump passage opens to a side surface of the smart vial adapter 24 and communicates with the air pump 26. The air pump 26 then routes the air through the air passage 27 and forces the air into the inner lumen 136 of the spike 118.

A smaller annular cavity 144 is formed in surrounding relationship with, and opening into, the inner lumen 136 of the spike 118. This cavity contains one or more electronic flow sensors 146, which are capable of measuring liquid flow within the lumen 136 so that the volume of the liquid drug passing through the lumen 136 during syringe filling can be measured or calculated. This allows the smart vial adapter 24 to perform its dose capture function (i.e., to determine how much of the liquid drug is withdrawn from the vial, and by inference how much of the liquid drug is injected by the user, at a particular time or during a particular interval). The flow sensors 146 are preferably hybrid thermal time of flight (TTOF) flow sensors of the type disclosed in detail in commonly assigned U.S. patent application Ser. No. 15/226,638, filed on Aug. 2, 2016, and published on Feb. 8, 2018 as U.S. Patent Application Publication No. 2018/0036495, which is incorporated herein by reference in its entirety. However, other types of thermal and non-thermal flow sensors can also be used.

During the last part of the syringe filling procedure described above, when the liquid drug is being drawn into the syringe barrel from the chamber 126 of the smart vial adapter 24, the chamber 126 is completely filled with the liquid medicament. As a result, the amount of liquid drug transferred from the chamber 126 into the syringe 50 is replaced by an equal amount of liquid drug that is drawn from the medicament vial 22 into the chamber 126 through the inner lumen 136 of the spike. Since the fluid passing through the lumen 136 flows past the flow sensors 146, this quantity can be calculated based on the measured flow rate and the elapsed time. The calculated quantity represents the dose of the drug that is transferred to the syringe 50 and injected by the user.

FIG. 11 also illustrates that the septum 128, instead of being solid, may be pre-formed with a slit 148 that allows it to be penetrated by a blunt cannula or Luer tip. This may be preferred when the drug that is withdrawn from the medication vial 22 is intended to be transferred to an IV line through a needleless valve or needleless injection site, rather than being injected into the skin with a needle. In this case, the syringe 50 of FIG. 10 is provided with a Luer fitting or blunt cannula, in lieu of the needle 54.

FIG. 12 is a schematic diagram of the electronic components 142 within the smart vial adapter 24 that perform the dose capture function just described, as well as other condition monitoring and information reporting functions. These components include a microcontroller 150 with an internal time-of-day clock, the previously described flow sensor(s) 146, a memory 152 for storing programming and data used by the microcontroller 150, a thermal sensor 154 for detecting the ambient temperature (and by inference the temperature of the medication vial 22 and its contents), an accelerometer 156 for measuring the amount of motion or perturbation the smart vial adapter 24 (and by inference the medication vial 22 and its contents) is subjected to, the air pump 26 that provides air pressure inside the medication vial 22, a Bluetooth module 158 for wirelessly communicating with the smartphone or other external electronic device (such as a computer or tablet) 32, one or more visual indicators 160 such as differently colored LEDs, one or more audible or tactile indicators 162 such as beepers, buzzers, speakers or vibrating devices, one or more pushbuttons 164, and a microswitch 166 that senses the initial connection of the vial adapter 16 to the vial 10. A power supply 168, typically in the form of a replaceable or rechargeable DC battery and suitable voltage regulating circuitry, activates and supplies power to the microcontroller 150 and to any of the other components of FIG. 12 that require electrical power.

Figure 9:
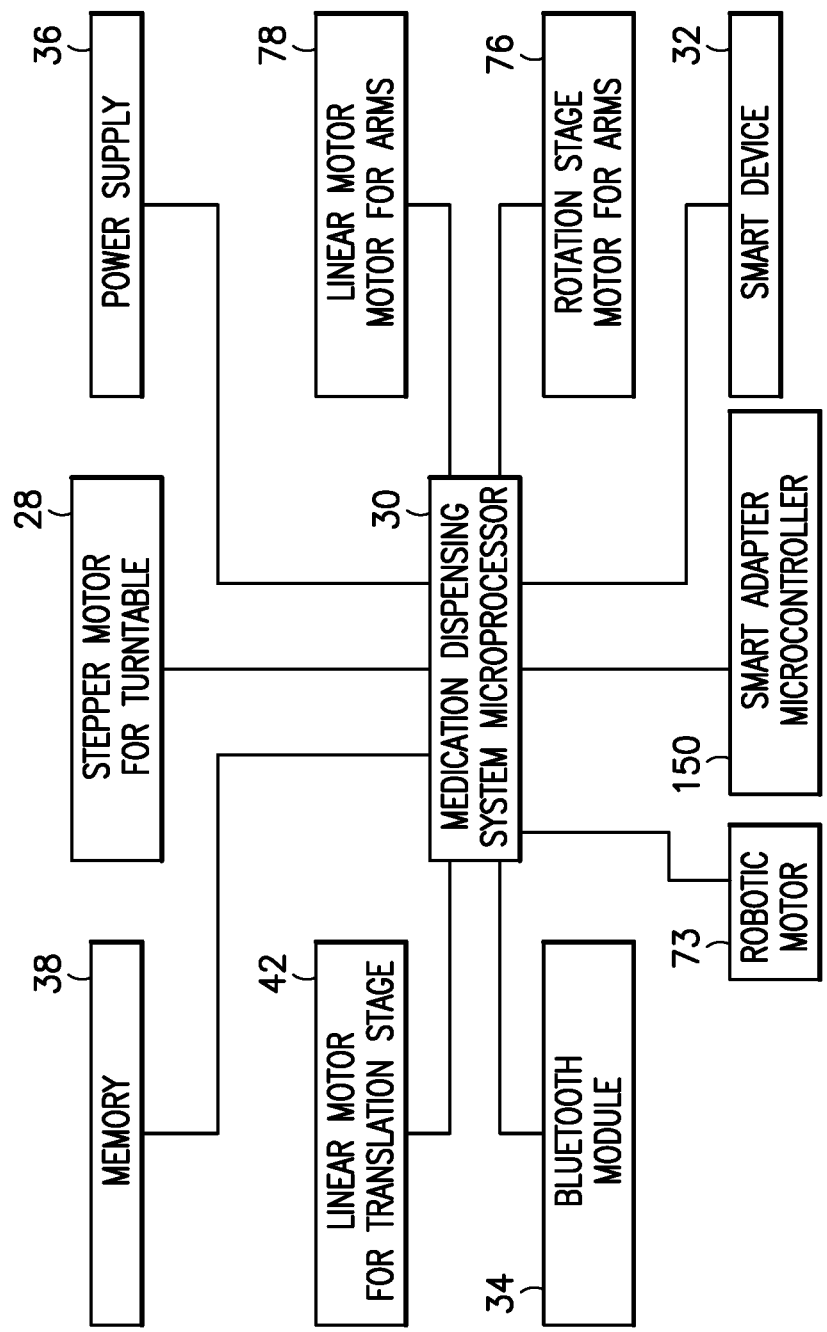
FIG. 9 illustrates a schematic diagram of the electronic components within the medication dispensing system of FIGS. 1-8.

FIGS. 2 and 9 illustrate various electrical components in the medication dispensing system 10. Specifically, these electrical components include a processor 30 configured to pair to the smart device 32, a Bluetooth module 34, a power supply 36 and memory 38. These electrical components are disposed in a rotation stage motor 76. The processor 30 is programmed to operate the medication dispensing system 10. Specifically, the processor 30 causes the turntable 20 to rotate, a translation stage 40 to axially move, a plurality of robotic arms 72*a*, 72*b*, 72*c* to clamp and let go of one of the syringes 50 and analyzes data received from the smart vial adapter 24. Further description and operation of the processor 30 is described in more detail below.

The Bluetooth module 34 provides wireless communication with a smart device such as the smartphone or other external electronic device (such as a computer or tablet) 32. The power supply 36 establishes electrical power between a power source (such as a battery or an a/c power source) and the medication dispensing system 10. The memory 38 stores data regarding the operation of the medication dispensing system 10. The memory 38 cooperates with the processor 30 to store data regarding movement of the turntable 20, the translation stage 40 and the syringes 50 while tracking medicament exchange from each of the smart vial adapter 24.

FIGS. 1-7 further illustrate the translation stage 40 that moves linearly in an XY plane. A linear motor 42, preferably Zaber X-LRQ-DE Series, powers the translation stage 40. The translation stage 40 carries a syringe rack 44. The syringe rack 44 carries the plurality of syringes 50. The translation stage 40 advantageously moves linearly to align one of the plurality of syringes 50 with one of the plurality of medication vials 22 carried by the turntable 20. The rotation of the turntable 20 and the axial movement of the translation stage 40 cooperate via instructions from the processor 30.

The plurality of syringes 50 each includes a shield 52, the needle 54, a flange 56 and the plunger 58. The shield 52 encloses and covers the needle 54 for each of the plurality of syringes 50. The shield 52 protects a user from accidental needle sticking prior to and after use of the syringe 50. The flange 56 is a widened surface from a body of the syringe 50 that allow the user to grip the syringe 50. As discussed above, the plunger 58 is pulled to draw medicament into the syringe 50. Conversely, the plunger 58 is depressed to expel medicament through the needle 54 of the syringe 50 and into a patient.

Figure 13:
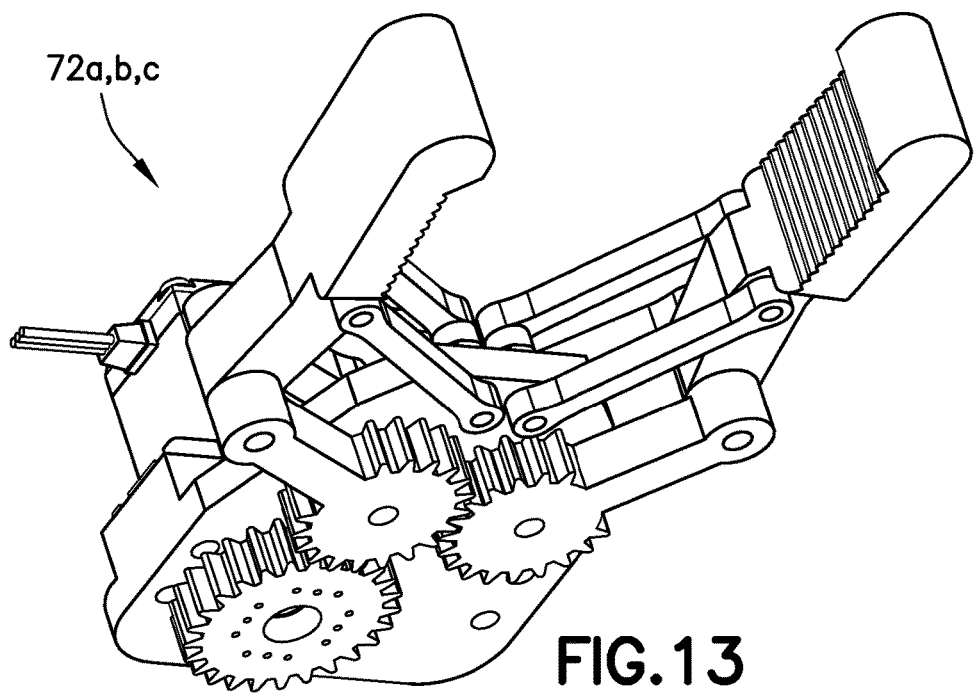
FIGS. 13-15 illustrate perspective views of robotic arms of FIGS. 1-7.
Figure 14:
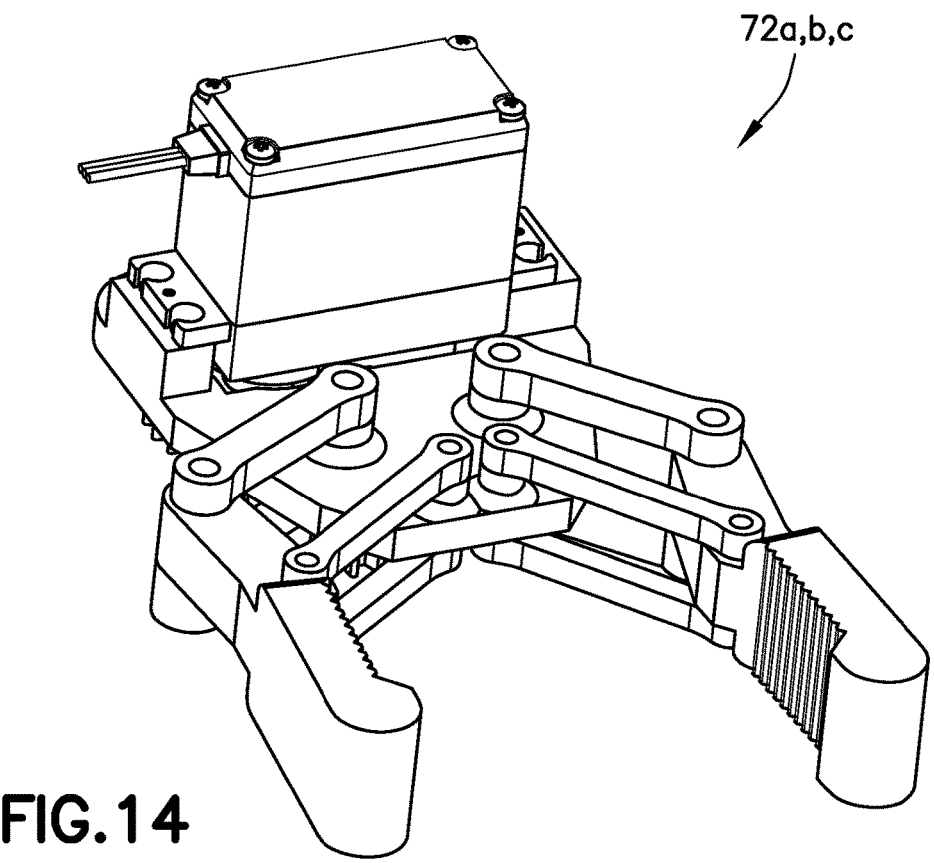
Figure 15:
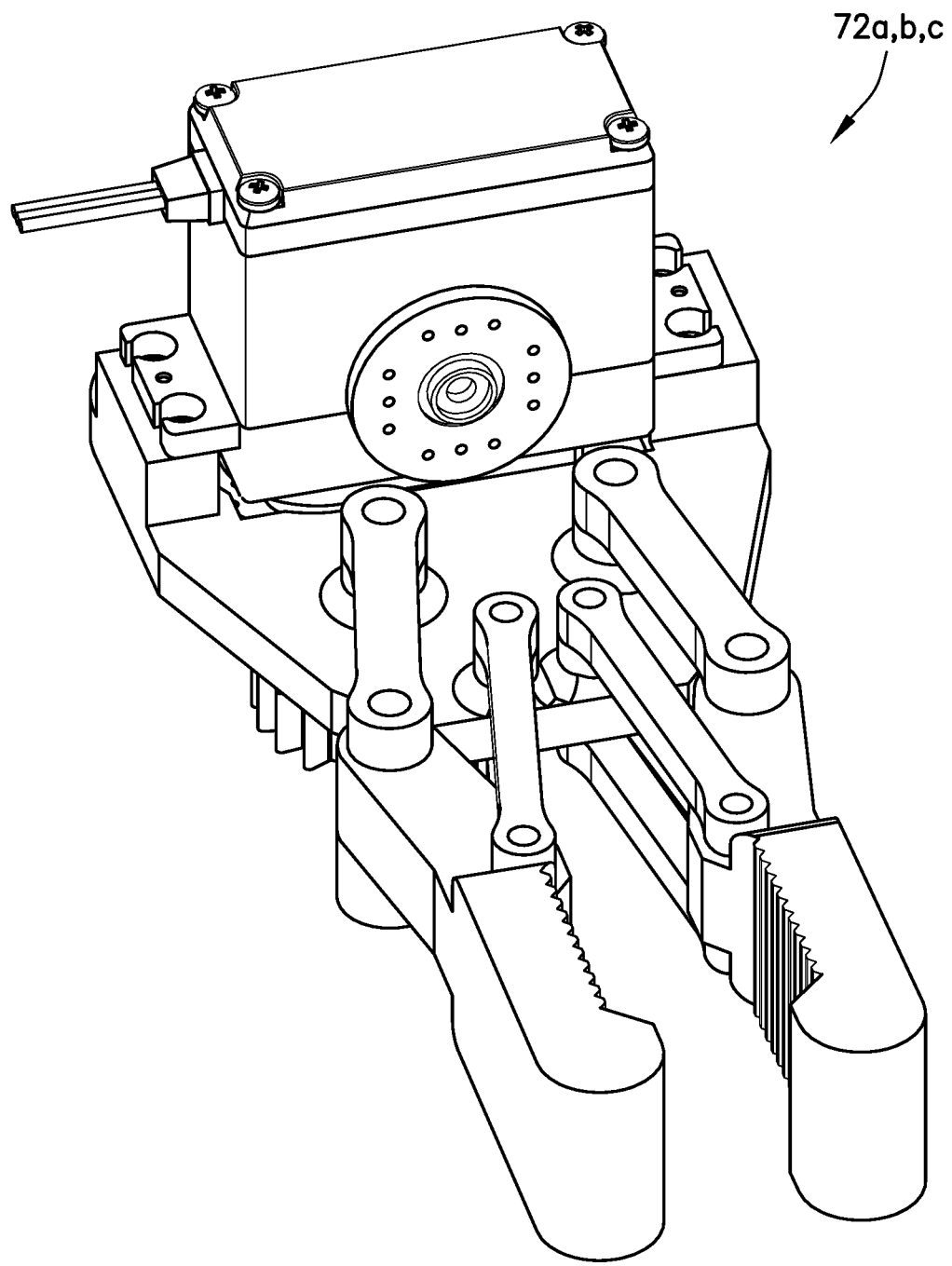

FIGS. 1-7 also illustrate a base 70 and a main beam 74 that supports and operates the medication dispensing system 10. Specifically, the base 70 supports the translation stage 40 as described above, as well as the rotation stage motor 76. The base 70 is connected to the main beam 74. The main beam 74 includes a plurality of tracks for one of a plurality of linear motors 78 to move and function. Each of the linear motors 78 and the rotation stage motor 76 are connected to one of a plurality of robotic arms 72a, 72b, 72c. FIGS. 13-15 illustrate the plurality of robotic arms 72a, 72b, 72c in the open and closed positions.

Figure 7:
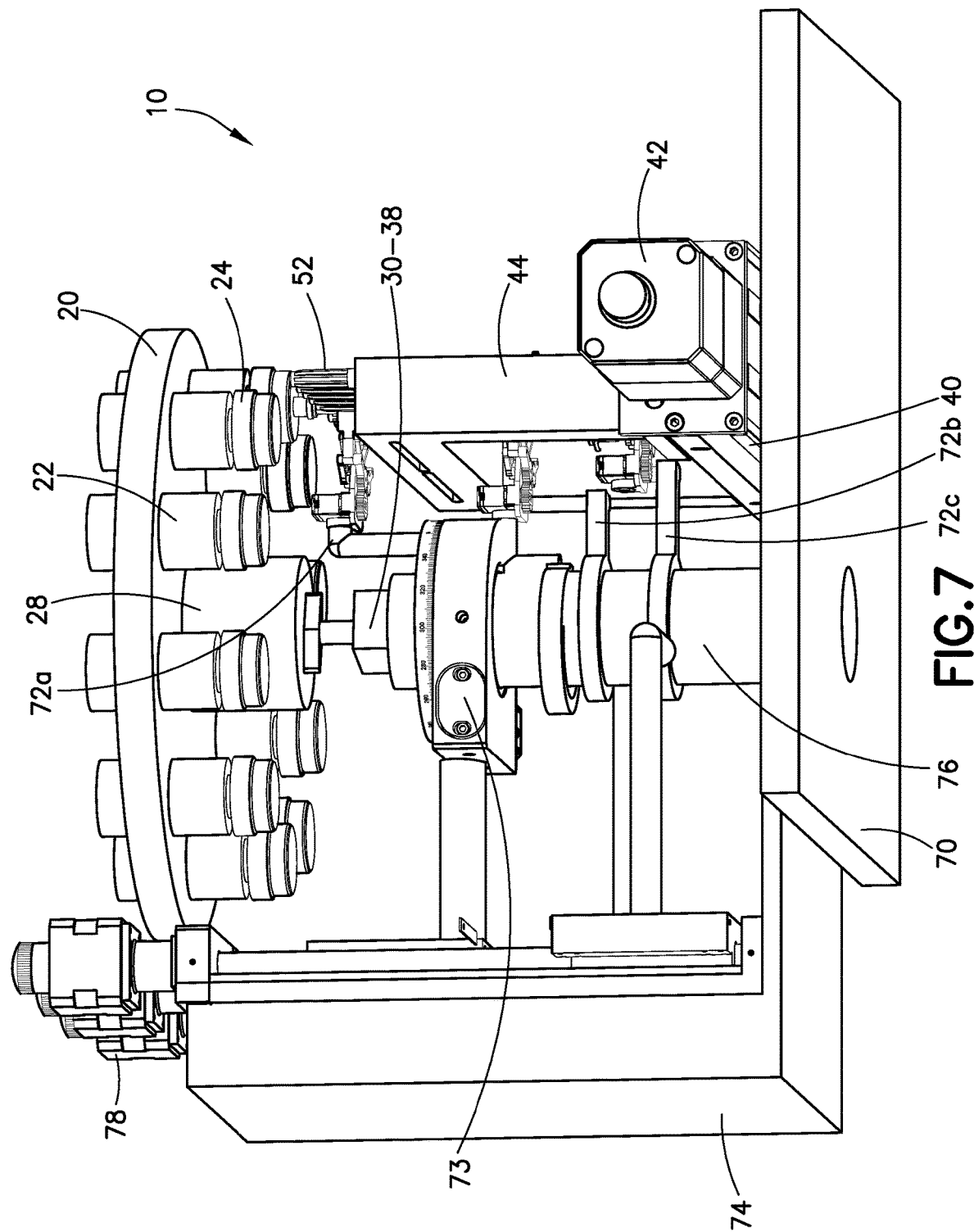
FIG. 7 illustrates a right side rear perspective view of the medication dispensing system of FIGS. 1-6.

FIGS. 2, 3 and 7 illustrate the tracks on the main beam 74 that the linear motors 78 traverses up and down. The linear motors 78 are each connected to a horizontal beam having a ring on its distal end. Each ring is connected to one of the plurality of robotic arms 72a, 72b, 72c. Each ring is disposed around the rotation stage motor 76 at different heights to fix the position of the linear motors 78 and the plurality of robotic arms 72a, 72b, 72c in the XY plane. The linear motors 78 move the plurality of robotic arms 72a, 72b, 72c upward and downward in the Z-axis. Specifically, the first robotic arm 72a is at a position higher than the second robotic arm 72b, and the second robotic arm 72b is at a position higher than the third robotic arm 72c.

The linear motors 78 further control each of the robotic arms 72a, 72b, 72c to open (FIGS. 13 and 14) and close (FIG. 15) for clamping and releasing the syringe 50. The first robotic arm 72a includes a robotic motor 73 that rotates the first robotic arm 72a. The first robotic arm 72a is the only robotic arm 72a, 72b, 72c that rotates. The overall operation and function of the robotic arms 72a, 72b, 72c is described below.

As further illustrated in FIG. 9, the processor 30 communicates to operate the electrical components described above, as well as the linear motor 42 in the translation stage 40, the smart adapter microcontroller 150 in the smart vial adapter 24, the rotation stage motor 76, the robotic motor 73 and the linear motor 78, which operate the plurality of robotic arms 72a, 72b, 72c. The processor 30 also provides commands to open (FIGS. 13 and 14) and close (FIG. 15) the robotic arms 72a, 72b, 72c.

Figure 8:
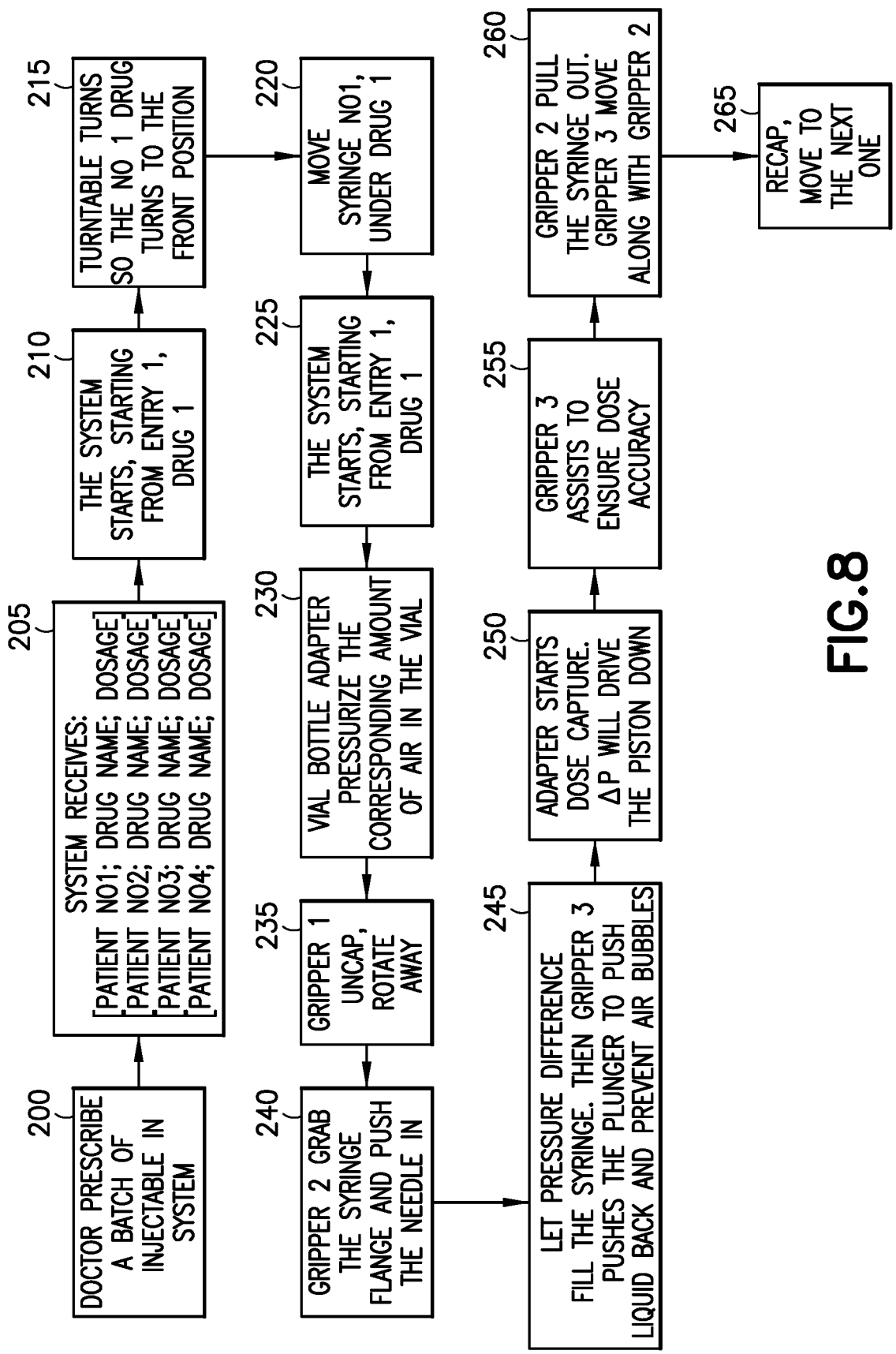
FIG. 8 illustrates a flow diagram of the operation of the medication dispensing system of FIGS. 1-7.

FIG. 8 illustrates a flowchart of the different steps during the operation of the medication dispensing system 10 and FIGS. 16-24 illustrates the different operational positions. In step 200, a clinician such as a doctor prescribes a batch of medicament, also known as an injectable and enters the prescription information into the smart device 32 paired to the medication dispensing system 10. In step 205, the medication dispensing system 105 receives prescription information including the patient and dose information from the smart device 32. For example, the prescription information received may include a name of the patient, a drug name, a dosage amount, a dosage schedule as to when the dosage is administered and at what frequency.

In step 210, the medication dispensing system 10 is reset to start at data entry number 1 carrying medication information for patient number 1. In step 215, the turntable 20 rotates so that the first, selected medication vial 22 is moved to the front position. At the same time, in step 220, the translation stage 40 is moved to the front position where the first, selected syringe 50 is aligned to the first, selected medication vial 22. In steps 225 and 230, the medication dispensing system 10 begins to prepare the first, selected medication vial 22 by sending a command from the processor 30 to the smart vial adapter 24 and pressurizing the selected medication vial 22 based on the received dosage amount. In an alternate embodiment, the selected medication vial 22 is not pressurized but rather dosage is manually transferred by pull the plunger 58 of the syringe 50.

Figure 16:
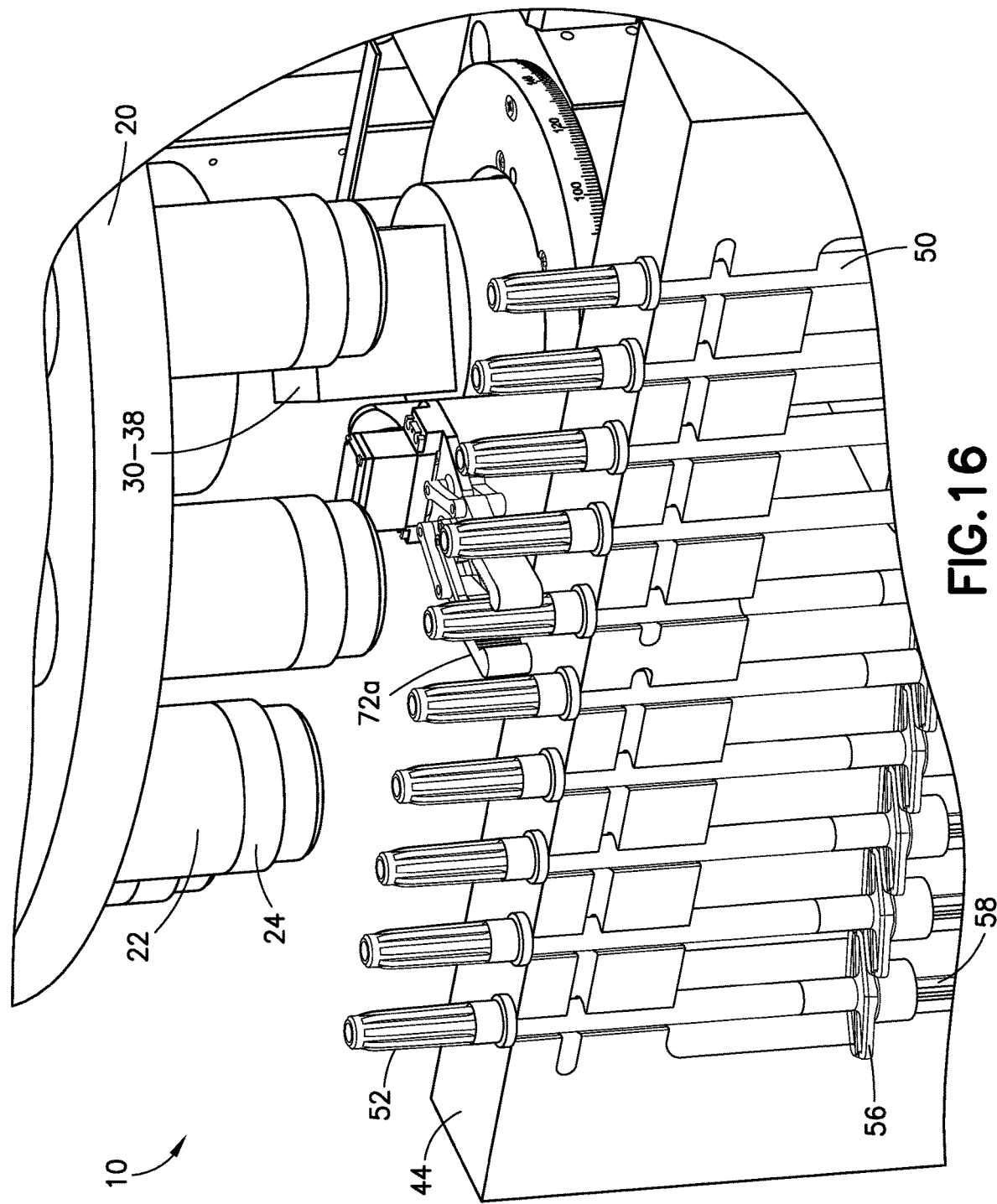
FIG. 16 illustrates one of the robotic arms capturing a shield of a syringe of FIGS. 1-7.
Figure 17:
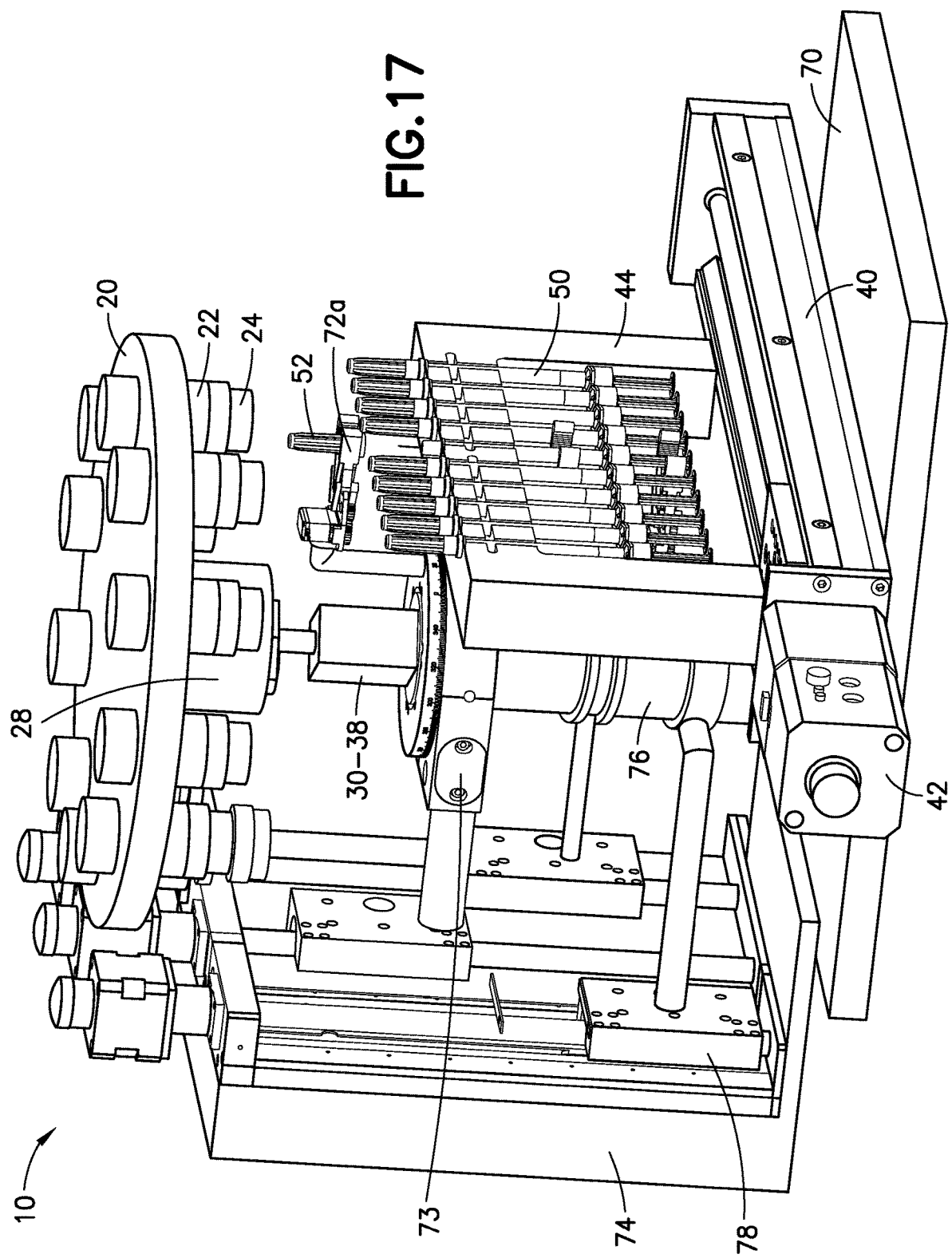
FIG. 17 illustrates one of the robotic arms removing the shield from the syringe of FIG. 16.
Figure 18:
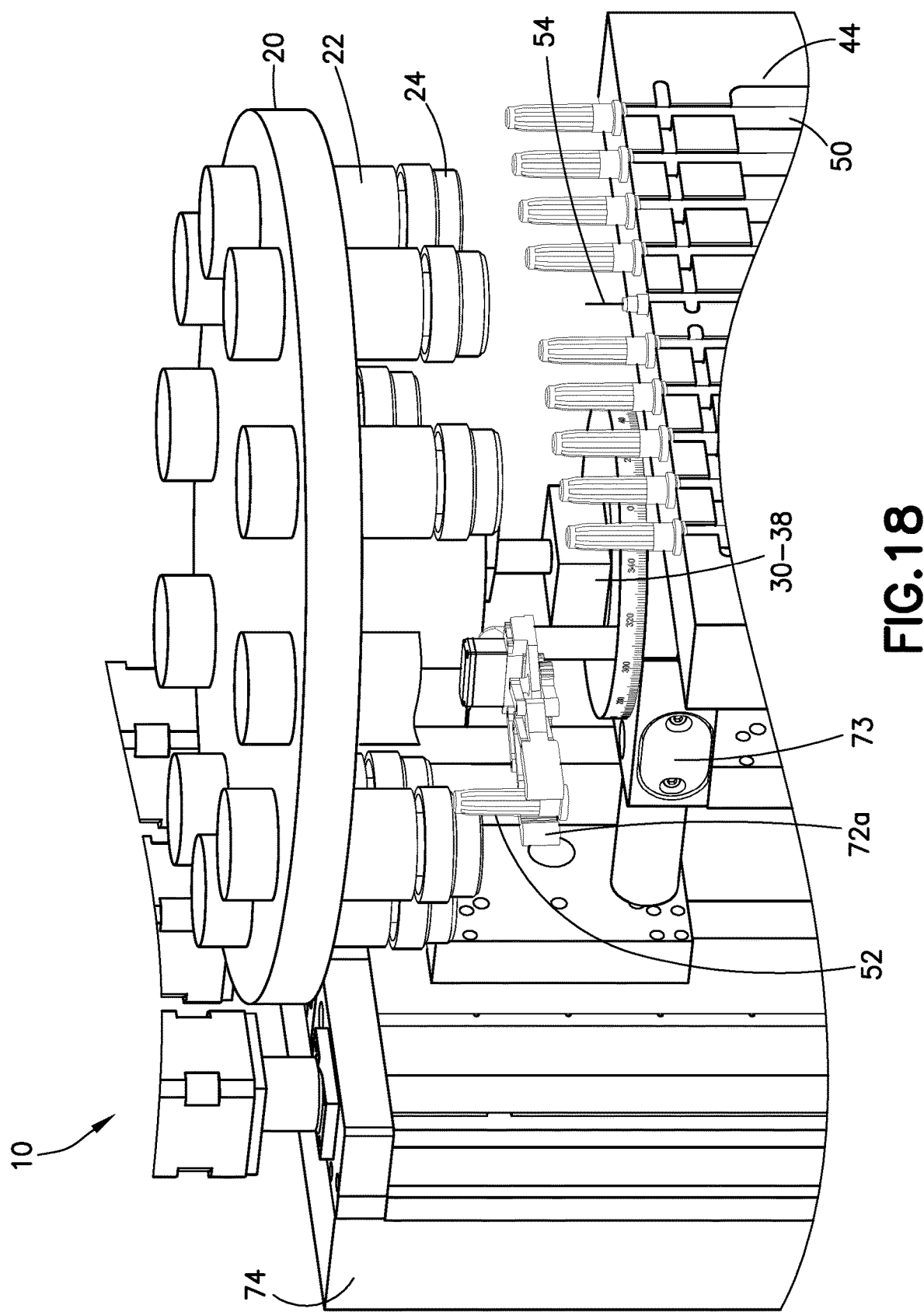
FIG. 18 illustrates one of the robotic arms rotating to move the shield away from the syringe of FIG. 17.

In step 235, as illustrated in FIGS. 16-18, the first robotic arm 72a grips the outer surface of the shield 52 of the selected syringe 50. Specifically, the processor 30 instructs the first robotic arm 72a to move from an open position to a closed, gripping position to grip the shield 52. FIG. 17 illustrates the processor 30 instructing the first robotic arm 72a to move the selected shield 52 upward to disengage and uncover the needle 54 of the selected syringe 50. The bottom of the selected shield 52 is disposed above a top surface of the remaining shields 52 covering the syringes 50. In this manner, the processor 30 instructs the robotic motor 73 to rotate the first robotic arm 72a and move the selected shield 52 away from the selected syringe 50.

Figure 19:
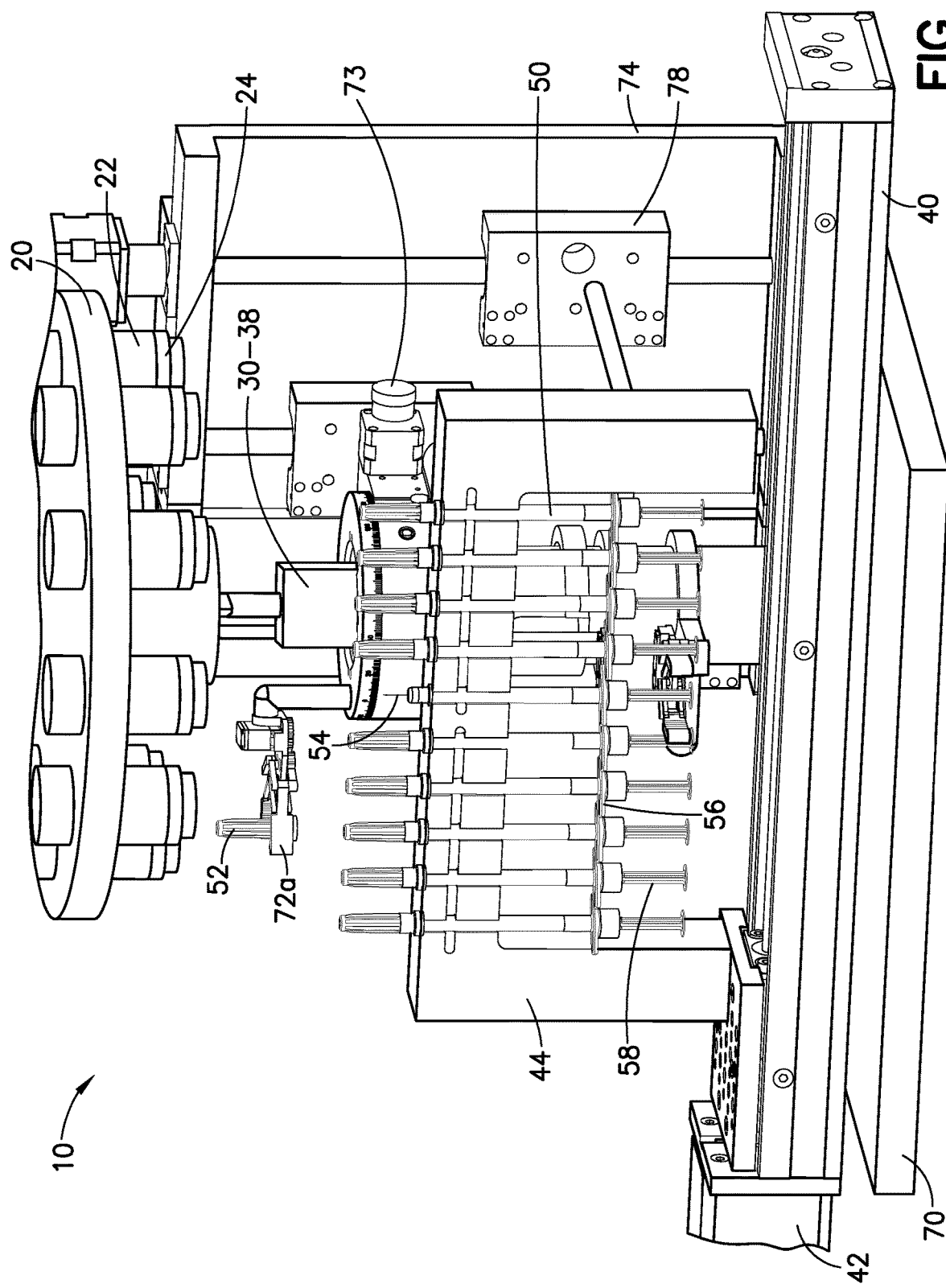
FIG. 19 illustrates a second robotic arm capturing a flange of the syringe of FIG. 18.
Figure 20:
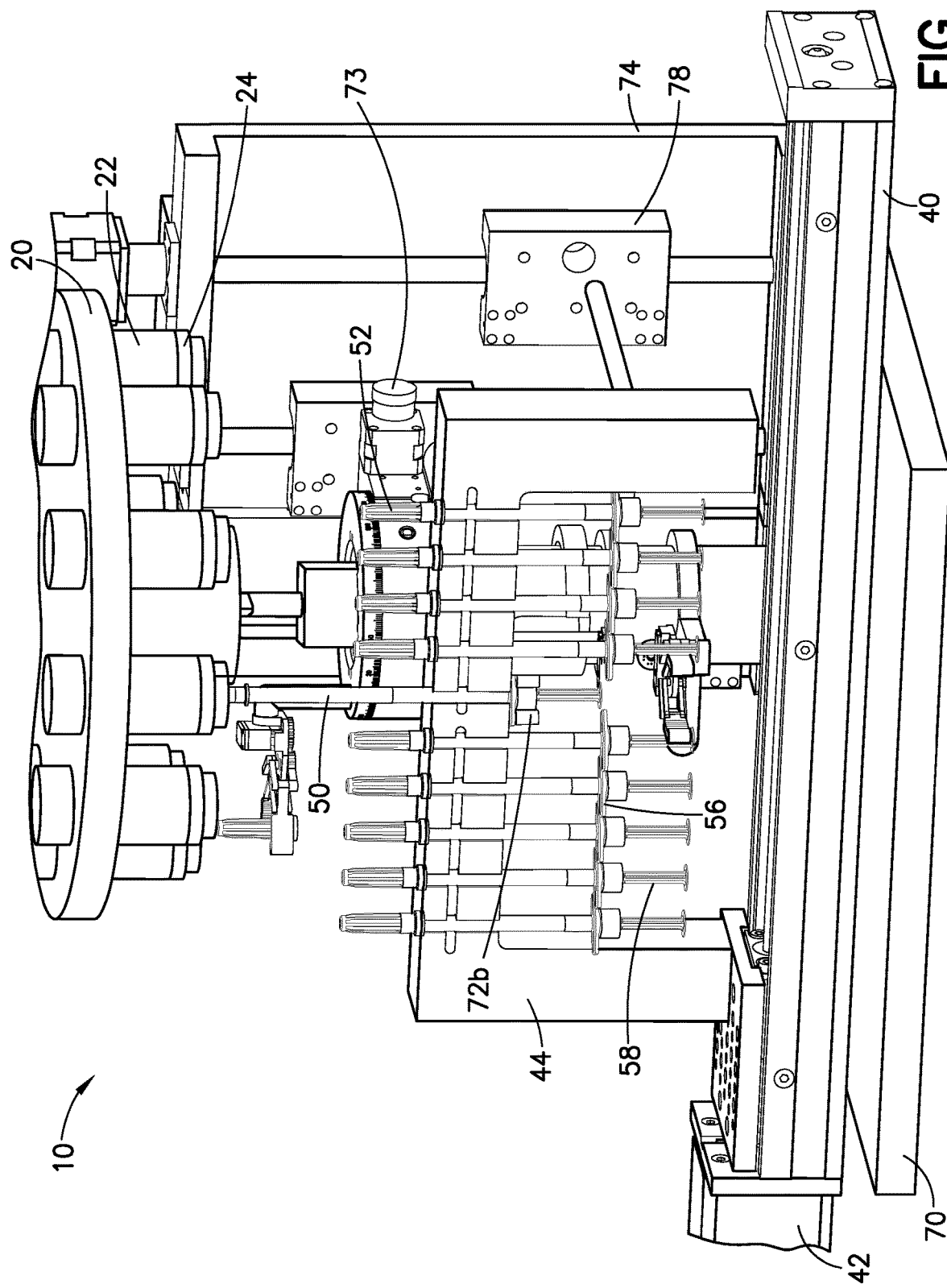
FIG. 20 illustrates the second robotic arm moving the syringe of FIG. 19 upward.

In step 240, as illustrated in FIG. 19, the processor 30 instructs the second robotic arm 72b to grip the flange 52 of the selected syringe 50. Subsequently, as illustrated in FIG. 20, the processor 30 instructs the linear motor 28 to move the second robotic arm 72b upward, thus moving the selected syringe 50 upward. During this movement, the needle 54 of the selected syringe 50 pierces the rubber septum 128 of the smart vial adapter 24 and enters into fluid communication with the medicament in the medication vial 22.

Figure 21:
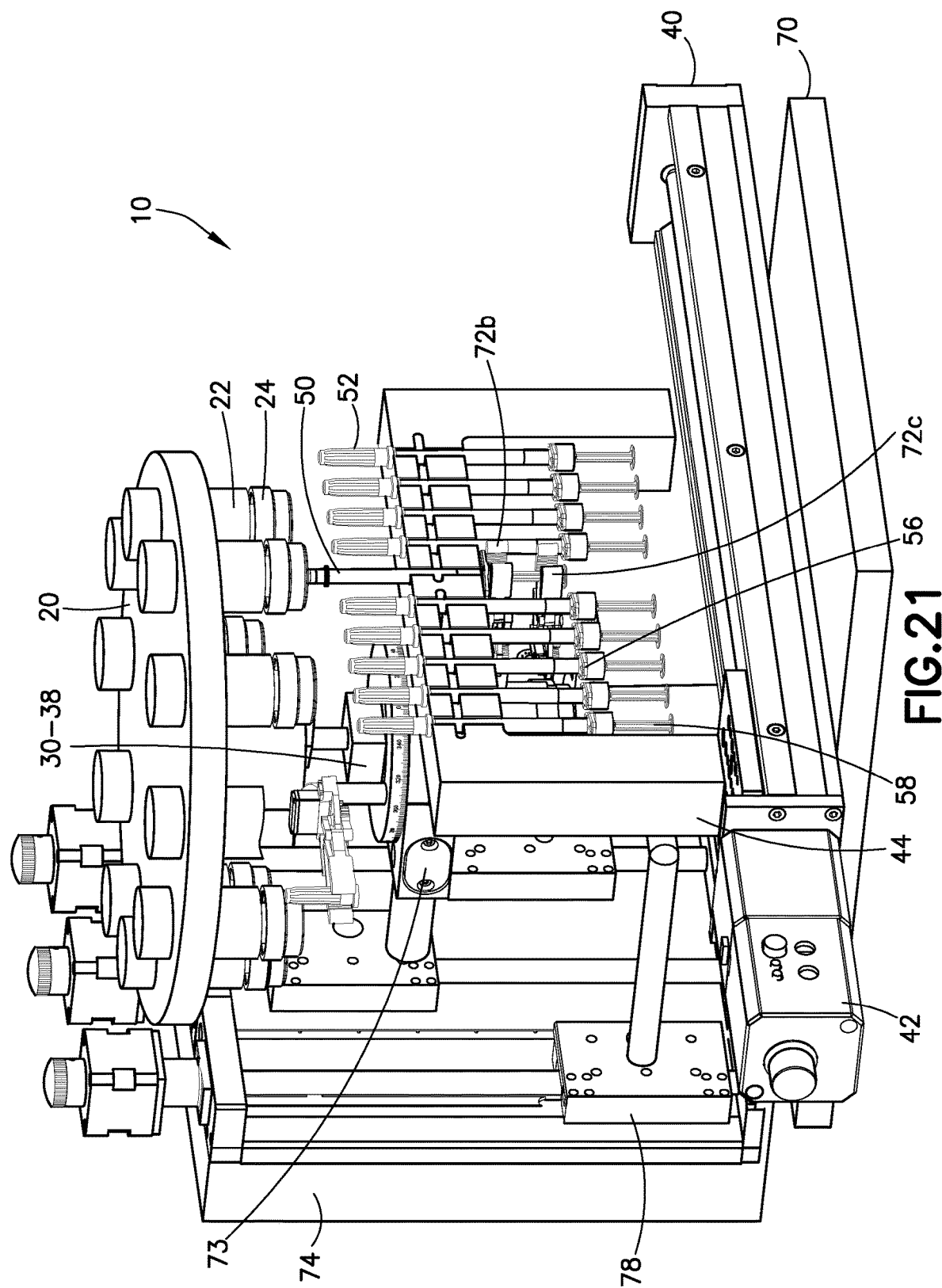
FIG. 21 illustrates a third robotic arm capturing a plunger rod of the syringe of FIG. 20.

In step 245, the pressurized, selected medication vial 22 transfers medicament to the selected syringe 50. After the pressure has equalized between the selected medication vial 22 and the atmospheric pressure, and no more medicament is being transferred from the medication vial 22 to the selected syringe 50, FIG. 21 illustrates the processor 30 instructing the third robotic arm 72c to grip the plunger 58 of the selected syringe 50. The third robotic arm 72c moves upward to push the transferred medicament back into the medication vial 22, thereby advantageously removing any accumulated air bubbles received in the selected syringe 50.

In step 250, the processor 30 instructs the third robotic arm 72c to release the plunger 58 of the selected syringe 50 and allows the smart vial adapter 24 to begin dose monitoring as the pressure drives the medicament flow back into the selected syringe 50. In step 255, after the pressure is equalized again, the processor 30 instructs the third robotic arm 72c to grip the plunger 58 of the selected syringe 50 to assist in ensuring dose accuracy. The processor 30 is able to identify the position of the plunger 58 for the third robotic arm 72c to grip based on monitored dosage received by the syringe 50 via the smart vial adapter 24.

Alternately, steps 245-255 are combined in such a way that the medication vial 22 is not pressurized and the third robotic arm 72c moves the plunger 58 of the selected syringe 50 downward to transfer the medicament dosage. This configuration can also be helpful if friction between an inner barrel of the syringe 50 and a rubber stopper of the plunger 58 is greater than the pressure in the medication vial 22 as described above.

Figure 22:
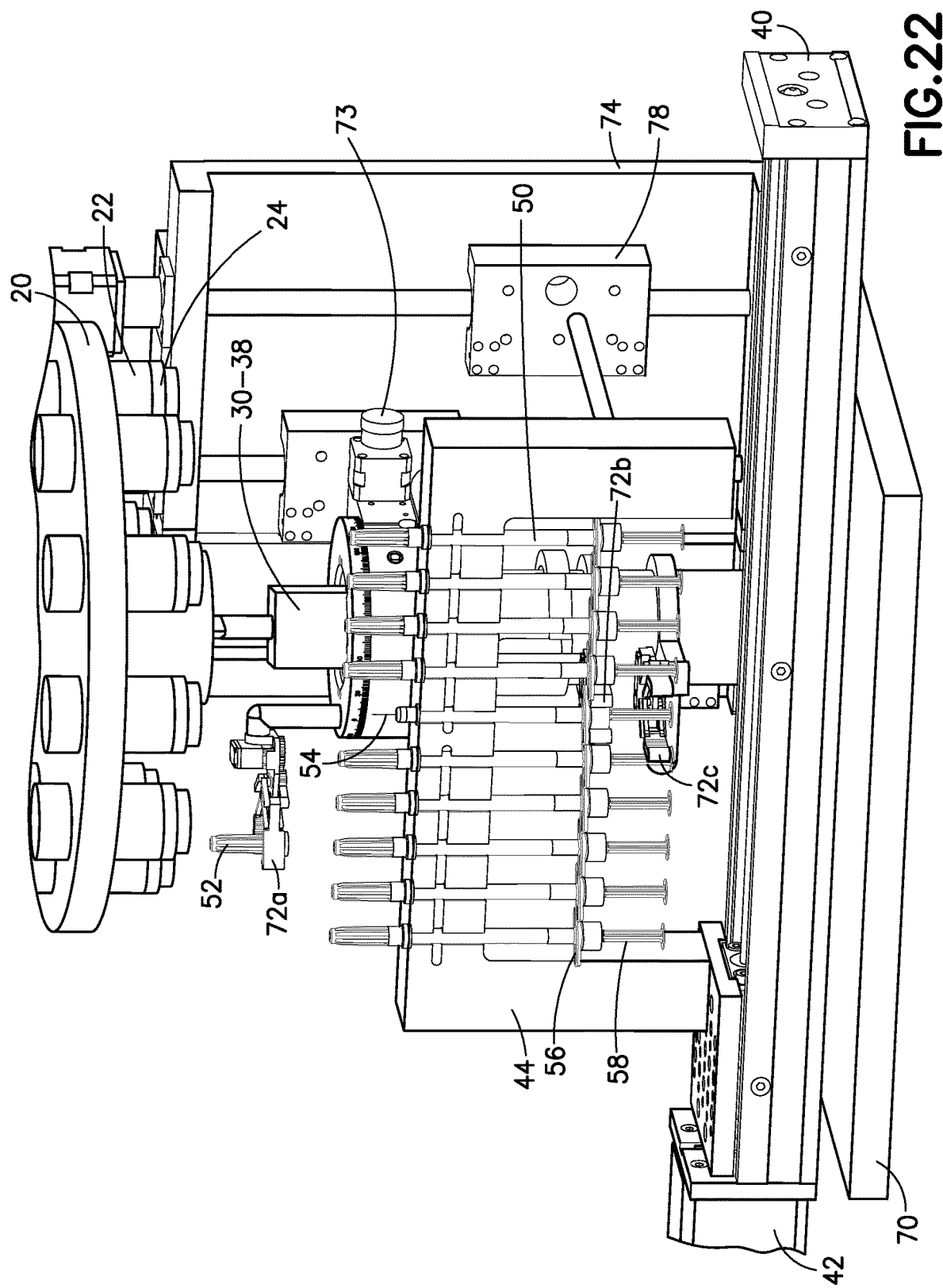
FIG. 22 illustrates the second robotic arm moving the syringe of FIG. 21 downward.

In step 260 as illustrated in FIG. 22, the processor 30 instructs the third robotic arm 72c to release the plunger 58, and the second robotic arm 72b to grip the flange 56 and move the selected syringe 50 downward. As a result, the selected syringe 50 is no longer engaged to the selected medication vial 22. That is, there is no more fluid communication between the selected syringe 50 and the selected medication vial 22 because the needle 54 of the selected syringe 50 does not pierce the septum 128 of the medication vial 22.

Figure 23:
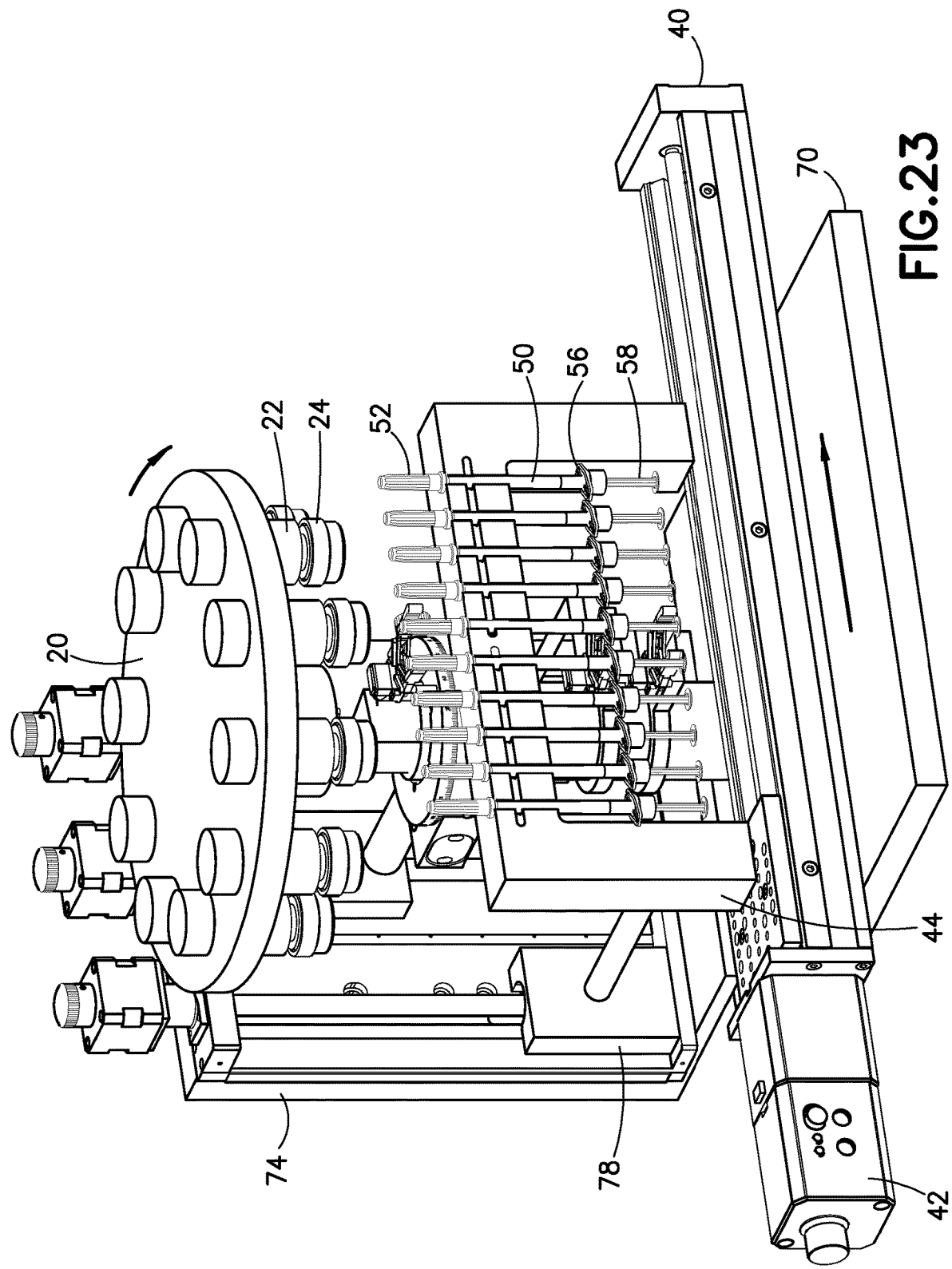
FIG. 23 illustrates the first robotic arm covering the needle of the syringe of FIG. 22.
Figure 24:
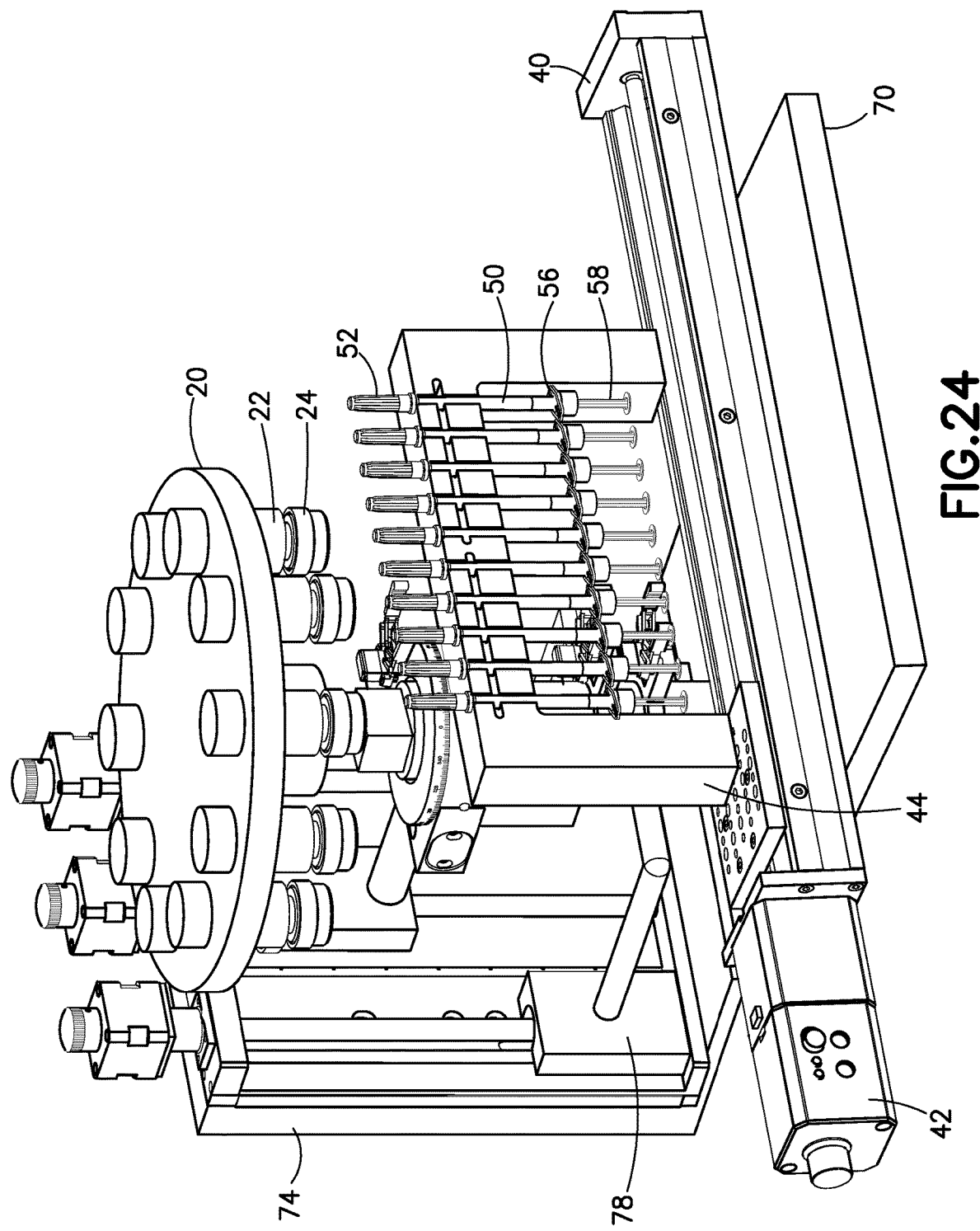
FIG. 24 illustrates the turntable rotating and a translation stage moving axially to align the next syringe with the next medication vial.

In step 265 as illustrated in FIG. 23, the processor 30 instructs the first robotic arm 72a, via the robotic motor 73, to recaps (covers or encloses) the needle 54 of the selected syringe 50 with the shield 52. Optionally, a label is created and placed on the selected syringe 50 to indicate that medicament transfer is complete and the label provides medicament and patient information.

Subsequently, the operation steps of the medication dispensing system 10 repeats by starting at step 215. Specifically, in step 215, the processor 30 instructs the rotation stage motor 76 to rotate the turntable 20 to the next selected medication vial 22 to the front position. The processor 30 also instructs the linear motor 42 to move the translation stage 40 to align the next, adjacent syringe 50 to the next selected medication vial 22. These process steps proceed and repeat for each syringe 50 carried by the syringe rack 44 and for each medication vial 22 carried by the turntable 20. The clinician can then replace the syringes 50 in the syringe rack 44 and the medication vial 22 in the turntable 20 to prepare another set of syringes 50 for medication delivery.

Accordingly, in the embodiments disclosed above, the medication dispensing system 10 advantageously relieves the burden from healthcare clinicians to manage many patients, various medications and injection schedules. The medication dispensing system 10 advantageously reduces errors in drug preparation and provides seamless medication delivery to patients. In addition, the automation in the medication dispensing system 10 advantageously provides efficient and timely preparation of the syringes.

Although only a few embodiments of the present invention have been shown and described, the present invention is not limited to the described embodiments. Instead, it will be appreciated by those skilled in the art that changes may be made to these embodiments without departing from the scope of the invention. In addition, any of the embodiments, features and/or elements disclosed herein may be combined with one another to form various additional combinations not specifically disclosed, as long as the embodiments, features and/or elements being combined do not contradict each other. All such changes and combinations are considered to be within the scope of the invention as defined by the appended claims and their equivalents.

What is claimed is:

1. A medication dispensing system configured to prepare a plurality of syringes for medication delivery, the system comprising:
   a turntable carrying a plurality of medication vials;
   a translation stage carrying a plurality of syringes, each syringe having a plunger and a needle, wherein the needle is enclosed by a cap;
   a base having a plurality of arms configured to interact with the plurality of syringes; and
   a processor that is programmed to rotate the turntable, axially move the translation stage and operate the plurality of arms such that a selected syringe of the plurality of syringes engages a selected medication vial of the plurality of medication vials to draw medicament; wherein
   the plurality of arms is configured to remove the cap of the selected syringe, move the selected syringe to establish fluid communication with the selected medication vial, move the plunger of the selected syringe away from the selected medication vial to draw the medicament into the selected syringe, and move the selected syringe to disengage from the selected medication vial.

2. The system of claim 1, wherein the plurality of medication vials is arranged concentrically on the turntable.

3. The system of claim 1, wherein the turntable rotates to align the selected medication vial with the selected syringe.

4. The system of claim 1, wherein:
   each medication vial is engaged to a smart vial adapter; and
   the smart vial adapter measures medicament information in each medication vial.

5. A medication dispensing system configured to prepare a plurality of syringes for medication delivery, the system comprising:
   a turntable carrying a plurality of medication vials, each medication vial being engaged to a smart vial adapter;
   a translation stage carrying a plurality of syringes;
   a base having a plurality of arms configured to interact with the plurality of syringes; and
   a processor that is programmed to rotate the turntable, axially move the translation stage and operate the plurality of arms such that a selected syringe of the plurality of syringes engages a selected medication vial of the plurality of medication vials to draw medicament; wherein
   the smart vial adapter is configured to carry out a dose capture, condition monitoring or information reporting function selected from the group consisting of measuring a quantity of the medicament drawn from the medication vial, measuring a time when the medicament is drawn from the medication vial, monitoring a temperature of the medication vial, measuring motion of the medication vial, producing a visual indication, producing an audible indication, and wirelessly communicating information to an external device.

6. The system of claim 1, wherein the translation stage includes a linear syringe rack carrying the plurality of syringes.

7. The system of claim 1, wherein the translation stage moves linearly to align the selected syringe with the selected medication vial.

8. The system of claim 1, wherein the plurality of arms is configured to cover the needle of the selected syringe with the shield.

9. The system of claim 1, wherein the selected medication vial is pressurized to transfer medicament upon engagement by the selected syringe.

10. The system of claim 1, wherein a label is placed on the selected syringe when medicament transfer is complete.

11. A method of preparing a plurality of syringes for medication delivery, the method comprising:
rotating a turntable to align a selected medication vial of a plurality of medication vials;
translating a translation stage linearly to align a selected syringe of a plurality of syringes to the selected medication vial;
programming a plurality of arms for:
removing a shield of the selected syringe;
moving the selected syringe toward the selected medication vial to pierce a septum of the selected medication vial with a needle of the selected syringe;
moving a plunger of the selected syringe to draw medicament into the selected syringe to transfer medicament from the selected medication vial to the selected syringe; and
disengaging the selected syringe from the selected medication vial.

12. The method of claim 11, further comprising repeating the rotating step for each medication vial of the plurality of medication vials to transfer medicament.

13. The method of claim 11, further comprising repeating the translating step for each syringe of the plurality of syringes to transfer medicament.

14. The method of claim 11, further comprising returning the shield over the needle of the selected syringe after the disengaging step.

15. The method of claim 11, further comprising disengaging the selected syringe from the selected vial by moving the selected syringe away from the selected vial.

16. The method of claim 11, further comprising sealing the selected medication vial via the septum when the selected syringe is disengaged from the selected medication vial.

17. The system of claim 4, wherein the measurement of medicament information by the smart vial adapter includes a function selected from the group consisting of measuring a quantity of the medicament drawn from the medication vial, measuring a time when the medicament is drawn from the medication vial, monitoring a temperature of the medication vial, measuring motion of the medication vial, producing a visual indication, producing an audible indication, and wirelessly communicating information to an external device.

* * * * *